US005430020A

United States Patent [19]

Schilling, Jr. et al.

[11] Patent Number: 5,430,020

[45] Date of Patent: Jul. 4, 1995

[54] RECOMBINANT ALVEOLAR SURFACTANT PROTEIN

[75] Inventors: James W. Schilling, Jr., Palo Alto; Robert T. White, Fremont; Barbara Cordell; Bradley J. Benson, both of San Francisco, all of Calif.

[73] Assignee: Scios Nova Inc., Mountain View, Calif.

[21] Appl. No.: 74,290

[22] Filed: Jun. 9, 1993

Related U.S. Application Data

[63] Continuation of Ser. No. 639,250, Jan. 7, 1991, abandoned, which is a continuation of Ser. No. 117,099, Nov. 4, 1987, abandoned, which is a continuation-in-part of Ser. No. 8,453, Jan. 29, 1987, abandoned, which is a continuation-in-part of Ser. No. 857,715, Apr. 30, 1986, Pat. No. 4,933,280, which is a continuation-in-part of Ser. No. 808,843, Dec. 13, 1985, Pat. No. 4,912,038, which is a continuation-in-part of Ser. No. 680,358, Dec. 11, 1984, Pat. No. 4,659,805.

[51] Int. Cl.$^6$ .......................... C07K 7/00; C07K 15/06

[52] U.S. Cl. ....................................... 514/12; 530/324; 530/350; 435/69.1

[58] Field of Search .................. 530/324, 350; 514/12; 435/69.1

[56] References Cited

U.S. PATENT DOCUMENTS

| | | | |
|---|---|---|---|
| 4,603,124 | 7/1986 | Takei et al. | 514/78 |
| 4,659,805 | 4/1987 | Schilling, Jr. et al. | 530/350 |
| 4,861,756 | 8/1989 | Jackson | 514/11 |
| 4,882,422 | 11/1989 | Taeusch et al. | 530/350 |
| 4,912,038 | 3/1990 | Schilling | 435/69.1 |
| 4,918,161 | 4/1990 | Stanbrink et al. | 530/324 |
| 5,055,553 | 10/1991 | Jacobs et al. | 530/300 |

FOREIGN PATENT DOCUMENTS

| | | | |
|---|---|---|---|
| WO87/06943 | 11/1987 | WIPO | 530/324 |

OTHER PUBLICATIONS

Olafson, R. et al., *Biochem. Biophys. Res. Commun.*, 148(3):1406–1411, Nov. 13, 1987.

Glasser, S. et al., *PNAS*, 84:4007–4011, Jun. 1987.

Hawgood, S., et al., *PNAS*, 84:66–70, Jan. 1987.

Jacobs, K. et al., *J. of Biol. Chem.*, issue of Jul. 15, 1987, pp. 9808–9811.

Whitsett, J. et al., *Pediatric Research*, 20(8):744–749, 1986.

Whitsett, J. et al., *Pediatric Research*, 20(5):460–467, 1986.

*Primary Examiner*—Jill Warden
*Assistant Examiner*—Benet Prickril
*Attorney, Agent, or Firm*—Morrison & Foerster

[57] ABSTRACT

The complete coding sequences and amino acid sequences for both canine and human 32K alveolar surfactant proteins (ASP) are disclosed; clones encoding variants of the SP-18 and SP-5 forms of human protein are disclosed. Methods and vectors for obtaining these proteins in recombinant form are also described. An improved method for purification of the 32K protein takes advantage of its carbohydrate affinity. Pharmaceutical compositions in the treatment of respiratory deficiency syndrome use the 10K proteins with or without the 32K form. Synthetic peptides based on the human SP-5 protein are provided as well, which peptides show significant ASP activity.

9 Claims, 16 Drawing Sheets

FIG. 1-1

Canine 18 Kd

```
|—— pd 18K-4
-180
Leu Leu Trp Leu Leu Leu Leu Pro Thr Leu Cys Gly Leu Gly Ala Ala Asp Trp Ser Ala Pro Ser Leu Ala Cys Ala Arg Gly Pro Ala
CTG CTG TGG CTG CTG CTG CTC CCC ACA CTG TGT GGC CTG GGT GCT GCT GAC TGG AGT GCC CCA TCC TTG GCT TGT GCC CGG GGC CCC GCA
                                                                 50

Phe Trp Cys Gln Ser Leu Glu Gln Ala Leu Gln Cys Arg Ala Leu Gly His Cys Leu Gln Glu Val Trp Gly Asn Ala Arg Ala Asp Asp
TTC TGG TGC CAA AGC CTG GAG CAA GCA CTG CAG TGC AGA GCC CTG GGT CAC TGT CTA CAG GAA GTC TGG GGC AAT GCA AGA GCT GAT GAC
        100                                                         150

Leu Cys Gln Glu Cys Gln Asp Ile Val Arg Ile Leu Thr Lys MET Thr Lys Glu Ala Ile Phe Gln Asp MET Val Arg Lys Phe Leu Glu
CTC TGC CAG GAA TGT CAG GAC ATC GTC CGC ATC CTC ACC AAG ATG ACC AAG GAG GCC ATC TTC CAG GAC ATG GTG CGG AAG TTC CTG GAG
                        200                                                         250
                                                                   |-> pd 18K-1
His Glu Cys Asp Val Leu Pro Leu Lys Leu Leu Thr Pro Gln Cys His His|MET Leu Gly Thr Tyr Phe Pro Val Val Val Asp Tyr Phe
CAT GAG TGT GAC GTT CTC CCC TTG AAG CTG CTC ACA CCC CAG TGC CAT CAC|ATG CTT GGC ACC TAC TTC CCA GTG GTG GTT GAC TAC TTC
                                    300                                                     350

Gln Ser Gln Ile Asn Pro Lys Ile Ile Cys Lys His Leu Gly Leu Cys Lys Pro Gly Leu Pro Glu Pro Glu Gln Glu Ser Glu Leu Ser
CAA AGC CAG ATT AAC CCA AAG ATC ATC TGT AAG CAC CTG GGC CTG TGC AAG CCT GGG CTT CCA GAG CCA GAG CAA GAG TCA GAG CTG TCA
                                                400                                                             450
                                                                                                                 -1
Asp Pro Leu Leu Asp Lys Leu Ile Leu Pro Glu Leu Pro Gly Ala Leu Gln Val Thr Gly Pro His Thr Gln Asp Leu Ser Glu Gln Gln
GAT CCG CTG CTG GAC AAG CTG ATC CTC CCT GAG CTG CCT GGA GCC CTC CAG GTG ACT GGA CCT CAT ACA CAG GAT CTC TCT GAG CAG CAG
                                                                 500
↓ 1
Leu Pro Ile Pro Leu Pro Tyr Cys Trp Leu Cys Arg Thr Leu Ile Lys Arg Ile Gln Ala MET Ile Pro Lys Gly Val Leu Ala Val Thr
TTG CCC ATC CCC CTC CCA TAC TGC TGG CTC TGC AGG ACT CTG ATC AAG CGG ATC CAA GCT ATG ATT CCC AAG GGT GTG CTG GCT GTG ACT
        550                                                         600
```

Val Gly Gln Val Cys His Val Val Pro Leu Val Val Gly Gly Ile Cys Gln Cys Leu Gly Glu Arg Tyr Thr Val Leu Leu Leu Asp Ala
GTG GGC CAG GTG TGC CAC GTC GTA CCC CTG GTG GTG GGC GGC ATC TGC CAG TGT CTC GGC GAG CGC TAC ACT GTC CTG CTC CTG GAT GCG
650 700 pd 18K-4

Leu Leu Gly Arg MET Leu Pro Gln Leu Val Cys Gly Leu Val Leu Arg Cys Ser His Glu Asp Ser Ala Gly Pro Ala Leu Ala Ser Leu
CTG CTG GGC CGC ATG CTG CCC CAG CTG GTC TGC GGC CTC GTC CTC CGG TGC TCC CAC GAG GAC AGC GCT GGG CCA GCT CTG GCG TCT CTG
750 800

Pro Ser Glu Trp Ser Pro Gln Glu Ser Lys Cys Gln Leu Cys MET Phe Val Thr Thr Gln Ala Gly Asn His Ser Glu Gln Ala Thr Pro
CCC AGT GAA TGG TCA CCC CAA GAG TCC AAG TGC CAG CTC TGC ATG TTT GTA ACC ACC CAG GCA GGG AAC CAC AGT GAG CAG GCC ACA CCA
850 900

Gln Ala Ile Arg Gln Ala Cys Leu Ser Ser Trp Leu Asp Arg Gln Lys Cys Glu Gln Phe Val Glu Gln His MET Pro Arg Leu Gln Thr
CAG GCA ATA CGC CAG GCC TGC CTC AGC TCC TGG CTG GAC AGA CAG AAG TGC GAG CAG TTT GTG GAG CAG CAC ATG CCT CGG CTG CAG ACC
950

Leu Ala Ser Gly Gly Arg Asp Ala His Thr Thr Cys Gln Ala Leu Gly Ala Cys Arg Thr Thr Phe Ser Pro Leu Gln Cys Ile His Ile
CTA GCA TCC GGG GGC AGG GAT GCC CAC ACC ACC TGC CAG GCC CTG GGG GCG TGT AGG ACC ACG TTC AGT CCT CTC CAG TGT ATC CAC ATT
1050

183
Pro His Phe End
CCT CAC TTC TGA CAAGGACT CAAAGCCATG CCAGCCCAAA CCAGAGCCAC TTCCTTGTGA GGTGCAGCCA AGGCAGCACC CTCTGGAGGA GATCCGCAAG AGGGGA
1100 1150

CTTC CGGCCTGATA ACTTCCGGCC AGAACTCACA CCCAACTGGA GCCAGGCCAG CTCCCGTAAC CCCCCAGCGC TGGGTCCAGG GAACACATCA GCCACATGGC CCTT
1200 1250

CCCTGG CTTGATTCCC TTTCATCTCC ATGTGCATAA GACACTAGCT TTTACAGTTA TTTTGCTAAT ACTTTCATAA AACTTAAATT CAGGAGAATA AAAAATGGGA CC
1300 1350 1400 pd 18K-1

ATGAAGTA CCGTAGAAGA TAGATATACT GAGAGCAAGCTT

Human SP18 cDNA #3

```
                                                   GAATTCGGGTGCC ATG GCT GAG TCA CAC CTG CTG CAG TGG CTG CTG CTG CTG CTG CCC ACG
                                                                 MET Ala Glu Ser His Leu Leu Gln Trp Leu Leu Leu Leu Leu Pro Thr
                                                                  1
                                                        100
CTC TGT GGC CCA GGC ACT GCT GCC TGG ACC ACC TCA TCC TTG GCC TGT GCC CAG GGC CCT GAG TTC TGG TGC CAA AGC CTG GAG CAA GCA
Leu Cys Gly Pro Gly Thr Ala Ala Trp Thr Thr Ser Ser Leu Ala Cys Ala Gln Gly Pro Glu Phe Trp Cys Gln Ser Leu Glu Gln Ala

                                                                      200
TTG CAG TGC AGA GCC CTA GGG CAT TGC CTA CAG GAA GTC TGG GGA CAT GTG GGA GCC GAT GAC CTA TGC CAA GAG TGT GAG GAC ATC GTC
Leu Gln Cys Arg Ala Leu Gly His Cys Leu Gln Glu Val Trp Gly His Val Gly Ala Asp Asp Leu Cys Gln Glu Cys Glu Asp Ile Val

                                                                                  300
CAC ATC CTT AAC AAG ATG GCC AAG GAG GCC ATT TTC CAG GAC ACG ATG AGG AAG TTC CTG GAG CAG GAG TGC AAC GTC CTC CCC TTG AAG
His Ile Leu Asn Lys MET Ala Lys Glu Ala Ile Phe Gln Asp Thr MET Arg Lys Phe Leu Glu Gln Glu Cys Asn Val Leu Pro Leu Lys

                                                                                              400
CTG CTC ATG CCC CAG TGC AAC CAA GTG CTT GAC GAC TAC TTC CCC CTG GTC ATC GAC TAC TTC CAG AAC CAG ATT GAC TCA AAC GGC ATC
Leu Leu MET Pro Gln Cys Asn Gln Val Leu Asp Asp Tyr Phe Pro Leu Val Ile Asp Tyr Phe Gln Asn Gln Ile Asp Ser Asn Gly Ile
                                                                                                    131
                                                                                                          500
TGT ATG CAC CTG GGC CTG TGC AAA TCC CGG CAG CCA GAG CCA GAG CAG GAG CCA GGG ATG TCA GAC CCC CTG CCC AAA CCT CTG CGG GAC
Cys MET His Leu Gly Leu Cys Lys Ser Arg Gln Pro Glu Pro Glu Gln Glu Pro Gly MET Ser Asp Pro Leu Pro Lys Pro Leu Arg Asp

                                                                                                                     600
CCT CTG CCA GAC CCT CTG CTG GAC AAG CTC GTC CTC CCT GTG CTG CCC GGG GCC CTC CAG GCG AGG CCT GGG CCT CAC ACA CAG GAT CTC
Pro Leu Pro Asp Pro Leu Leu Asp Lys Leu Val Leu Pro Val Leu Pro Gly Ala Leu Gln Ala Arg Pro Gly Pro His Thr Gln Asp Leu
```

```
TCC GAG CAG CAA TTC CCC ATT CCT CTC CCC TAT TGC TGG CTC TGC AGG GCT CTG ATC AAG CGG ATC CAA GCC ATG ATT CCC AAG GGT GCG
Ser Glu Gln Gln Phe Pro Ile Pro Leu Pro Tyr Cys Trp Leu Cys Arg Ala Leu Ile Lys Arg Ile Gln Ala MET Ile Pro Lys Gly Ala
            200 201
        700
CTA CGT GTG GCA GTG GCC CAG GTG TGC CGC GTG GTA CCT CTG GTG GCG GGC GGC ATC TGC CAG TGC CTG GCT GAG CGC TAC TCC GTC ATC
Leu Arg Val Ala Val Ala Gln Val Cys Arg Val Val Pro Leu Val Ala Gly Gly Ile Cys Gln Cys Leu Ala Glu Arg Tyr Ser Val Ile

              800
CTG CTC GAC ACG CTG CTG GGC CGC ATG CTG CCC CAG CTG GTC TGC CGC CTC GTC CTC CGG TGC TCC ATG GAT GAC AGC GCT GGC CCA AGG
Leu Leu Asp Thr Leu Leu Gly Arg MET Leu Pro Gln Leu Val Cys Arg Leu Val Leu Arg Cys Ser MET Asp Asp Ser Ala Gly Pro Arg
                                                                                                                    286
                         900
TCG CCG ACA GGA GAA TGG CTG CCG CGA GAC TCT GAG TGC CAC CTC TGC ATG TCC GTG ACC ACC CAG GCC GGG AAC AGC AGC GAG CAG GCC
Ser Pro Thr Gly Glu Trp Leu Pro Arg Asp Ser Glu Cys His Leu Cys MET Ser Val Thr Thr Gln Ala Gly Asn Ser Ser Glu Gln Ala
287
                                                     1000
ATA CCA CAG GCA ATG CTC CAG GCC TGT GTT GGC TCC TGG CTG GAC AGG GAA AAG TGC AAG CAA TTT GTG GAG CAG CAC ACG CCC CAG CTG
Ile Pro Gln Ala MET Leu Gln Ala Cys Val Gly Ser Trp Leu Asp Arg Glu Lys Cys Lys Gln Phe Val Glu Gln His Thr Pro Gln Leu

                                                                  1100
CTG ACC CTG GTG CCC AGG GGC TGG GAT GCC CAC ACC ACC TGC CAG GCC CTC GGG GTG TGT GGG ACC ATG TCC AGC CCT CTC CAG TGT ATC
Leu Thr Leu Val Pro Arg Gly Trp Asp Ala His Thr Thr Cys Gln Ala Leu Gly Val Cys Gly Thr MET Ser Ser Pro Leu Gln Cys Ile

                                                                    1200
CAC AGC CCC GAC CTT TGA TGAGAACTCAG CTGTCCAGAA AAAGACACGT CCTTTAAAAT GCTGCAGTAT GGCCAGACAG TGGTGGCTCA CACCTGCAAT CCCAGC
His Ser Pro Asp Leu End
                    381

ACCT TAGGAGGCCG AGGCAGGAGG ATCC
```

Exons of Human SP18 gene

```
                  1041
Exon I    ...agag GTGCC ATG GCT GAG TCA CAC CTG CTG CAG TGG CTG CTG CTG CTG CTG CCC ACG CTC TGT GGC CCA GGC ACT G gtga...
                        MET Ala Glu Ser His Leu Leu Gln Trp Leu Leu Leu Leu Leu Pro Thr Leu Cys Gly Pro Gly Thr A
                         1
                  1423
Exon II   ...acag CT GCC TGG ACC ACC TCA TCC TTG GCC TGT GCC CAG GGC CCT GAG TTC TGG TGC CAA AGC CTG GAG CAA GCA TTG CAG
                  la Ala Trp Thr Thr Ser Ser Leu Ala Cys Ala Gln Gly Pro Glu Phe Trp Cys Gln Ser Leu Glu Gln Ala Leu Gln

                  TGC AGA GCC CTA GGG CAT TGC CTA CAG GAA GTC TGG GGA CAT GTG GGA GCC gtga...
                  Cys Arg Ala Leu Gly His Cys Leu Gln Glu Val Trp Gly His Val Gly Ala

                  2052
Exon III  ...ccag GAT GAC CTA TGC CAA GAG TGT GAG GAC ATC GTC CAC ATC CTT AAC AAG ATG GCC AAG GAG GCC ATT TTC CAG gtaa...
                  Asp Asp Leu Cys Gln Glu Cys Glu Asp Ile Val His Ile Leu Asn Lys MET Ala Lys Glu Ala Ile Phe Gln

                  2478
Exon IV   ...ccag GAC ACG ATG AGG AAG TTC CTG GAG CAG GAG TGC AAC GTC CTC CCC TTG AAG CTG CTC ATG CCC CAG TGC AAC CAA GTG
                  Asp Thr MET Arg Lys Phe Leu Glu Gln Glu Cys Asn Val Leu Pro Leu Lys Leu Leu MET Pro Gln Cys Asn Gln Val

                  CTT GAC GAC TAC TTC CCC CTG GTC ATC GAC TAC TTC CAG AAC CAG ACT gtga...
                  Leu Asp Asp Tyr Phe Pro Leu Val Ile Asp Tyr Phe Gln Asn Gln Thr
                                                                              131
                  3431
Exon V    ...ccag GAC TCA AAC GGC ATC TGT ATG CAC CTG GGC CTG TGC AAA TCC CGG CAG CCA GAG CCA GAG CAG GAG CCA GGG ATG TCA
                  Asp Ser Asn Gly Ile Cys MET His Leu Gly Leu Cys Lys Ser Arg Gln Pro Glu Pro Glu Gln Glu Pro Gly MET Ser

                  GAC CCC CTG CCC AAA CCT CTG CGG GAC CCT CTG CCA GAC CCT CTG CTG GAC AAG CTC GTC CTC CCT GTG CTG CCC GGG
                  Asp Pro Leu Pro Lys Pro Leu Arg Asp Pro Leu Pro Asp Pro Leu Leu Asp Lys Leu Val Leu Pro Val Leu Pro Gly

                  GCC CTC CAG GCG AGG CCT GGG CCT CAC ACA CAG gtga...
                  Ala Leu Gln Ala Arg Pro Gly Pro His Thr Gln
```

Exon VI

3847
...ccag GAT CTC TCC GAG CAG CAA TTC CCC ATT CCT CTC CCC TAT TGC TGG CTC TGC AGG GCT CTG ATC AAG CGG ATC CAA GCC
Asp Leu Ser Glu Gln Gln Phe Pro Ile Pro Leu Pro Tyr Cys Trp Leu Cys Arg Ala Leu Ile Lys Arg Ile Gln Ala
200 201
ATG ATT CCC AAG gtga...
MET Ile Pro Lys Exon VII 4599
...ccag GGT GCG CTA CGT GTG GCA GTG GCC CAG GTG TGC CGC GTG GTA CCT CTG GTG GCG GGC GGC ATC TGC CAG TGC CTG GCT
Gly Ala Leu Arg Val Ala Val Ala Gln Val Cys Arg Val Val Pro Leu Val Ala Gly Gly Ile Cys Gln Cys Leu Ala GAG CGC TAC TCC GTC ATC CTG CTC GAC ACG CTG CTG GGC CGC ATG CTG CCC CAG CTG GTC TGC CGC CTC GTC CTC CGG
Glu Arg Tyr Ser Val Ile Leu Leu Asp Thr Leu Leu Gly Arg MET Leu Pro Gln Leu Val Cys Arg Leu Val Leu Arg TGC TCC ATG GAT GAC AGC GCT GGC CCA A gtga...
Cys Ser MET Asp Asp Ser Ala Gly Pro A Exon VIII 4955
...ccag GG TCG CCG ACA GGA GAA TGG CTG CCG CGA GAC TCT GAG TGC CAC CTC TGC ATG TCC GTG ACC ACC CAG GCC GGG AAC
rg Ser Pro Thr Gly Glu Trp Leu Pro Arg Asp Ser Glu Cys His Leu Cys MET Ser Val Thr Thr Gln Ala Gly Asn
286 287
AGC AGC GAG CAG GCC ATA CCA CAG GCA ATG CTC CAG GCC TGT GTT GGC TCC TGG CTG GAC AGG GAA AAG gtat...
Ser Ser Glu Gln Ala Ile Pro Gln Ala MET Leu Gln Ala Cys Val Gly Ser Trp Leu Asp Arg Glu Lys Exon IX 6332
...tcag TGC AAG CAA TTT GTG GAG CAG CAC ACG CCC CAG CTG CTG ACC CTG GTG CCC AGG GGC TGG GAT GCC CAC ACC ACC TGC
Cys Lys Gln Phe Val Glu Gln His Thr Pro Gln Leu Leu Thr Leu Val Pro Arg Gly Trp Asp Ala His Thr Thr Cys CAG gtac...
Gln Exon X 6905
...acag GCC CTC GGG GTG TGT GGG ACC ATG TCC AGC CCT CTC CAG TGT ATC CAC AGC CCC GAC CTT TGA TGA GAACTCAGCT GTCC
Ala Leu Gly Val Cys Gly Thr MET Ser Ser Pro Leu Gln Cys Ile His Ser Pro Asp Leu End End
381

FIG. 3-2

| Oligo-nucleotide Probe No. | Sequence |
|---|---|
| 1 | ATC CCC TGC TTC CCC AGC AGC CTG AAG CGC CT<br>3'-TAG GGG ACG AAG GGG TCG TCG GAC TTC GCG GA-5' |
| 2 | ATC CCC TGC TTC CCC TCC AGC CTG AAG CGC CT<br>3'-TAG GGG ACG AAG GGG AGG TCG GAC TTC GCG GA-5' |
| 3 | ATC CCC TGC TTC CCC TCC TCC CTG AAG CGC CT<br>3'-TAG GGG ACG AAG GGG AGG AGG GAC TTC GCG GA-5' |
| 4 | ATC CCC TGC TTC CCC TCC TCC CTG AAG AGA CT<br>3'-TAG GGG ACG AAG GGG AGG AGG GAC TTC TCT GA-5' |
| 5 | ATC CCC TGC TTC CCC AGC TCC CTG AAG AGA CT<br>3'-TAG GGG ACG AAG GGG TCG AGG GAC TTC TCT GA-5' |
| 6 | ATC CCC TGC TTC CCC AGC TCC CTG AAG CGC CT<br>3'-TAG GGG ACG AAG GGG TCG AGG GAC TTC GCG GA-5' |

FIG. 4

Human SP5 cDNA #18

GAATTCGGGGAG AGCATAGCAC CTGCAGCAAG ATG GAT GTG GGC AGC AAA GAG GTC CTG ATG GAG AGC CCG CCG GAC TAC TCC GCA GCT
MET Asp Val Gly Ser Lys Glu Val Leu MET Glu Ser Pro Pro Asp Tyr Ser Ala Ala
1

100
CCC CGG GGC CGA TTT GGC ATT CCC TGC TGC CCA GTG CAC CTG AAA CGC CTT CTT ATC GTG GTG GTG GTG GTG GTC CTC ATC GTC GTG GTG
Pro Arg Gly Arg Phe Gly Ile Pro Cys Cys Pro Val His Leu Lys Arg Leu Leu Ile Val Val Val Val Val Val Leu Ile Val Val Val
24 25

200
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
65

300
CAA CGC CTG GCC CTG AGT GAG CAC CTG GTT ACC ACT GCC ACC TTC TCC ATC GGC TCC ACT GGC CTC GTG GTG TAT GAC TAC CAG CAG CTG
Gln Arg Leu Ala Leu Ser Glu His Leu Val Thr Thr Ala Thr Phe Ser Ile Gly Ser Thr Gly Leu Val Val Tyr Asp Tyr Gln Gln Leu
80 108

400
CTG ATC GCC TAC AAG CCA GCC CCT GGC ACC TGC TGC TAC ATC ATG AAG ATA GCT CCA GAG AGC ATC CCC AGT CTT GAG GCT CTC AAT AGA
Leu Ile Ala Tyr Lys Pro Ala Pro Gly Thr Cys Cys Tyr Ile MET Lys Ile Ala Pro Glu Ser Ile Pro Ser Leu Glu Ala Leu Asn Arg
138

500
AAA GTC CAC AAC TTC CAG ATG GAA TGC TCT CTG CAG GCC AAG CCC GCA GTG CCT ACG TCT AAG CTG GGC CAG GCA GAG GGG CGA GAT GCA
Lys Val His Asn Phe Gln MET Glu Cys Ser Leu Gln Ala Lys Pro Ala Val Pro Thr Ser Lys Leu Gly Gln Ala Glu Gly Arg Asp Ala

600
GGC TCA GCA CCC TCC GGA GGG GAC CCG GCC TTC CTG GGC ATG GCC GTG AAC ACC CTG TGT GGC GAG GTG CCG CTC TAC TAC ATC TAG GAC
Gly Ser Ala Pro Ser Gly Gly Asp Pro Ala Phe Leu Gly MET Ala Val Asn Thr Leu Cys Gly Glu Val Pro Leu Tyr Tyr Ile End
186 197

700
G CCTCCGGTGA GCAGGGTCAG TGGAAGCCCC AACGGGAAAG GAAACGCCCC GGGCAAAGGG TCTTTTGCAG CTTTTGCAGA CGGGCAAGAA GCTGCTTCTG CCCACAC

800
CGC AGGGACAAAC CCTGGAGAAA TGGGAGCTTG GGGAGAGGAT GGGAGTGGGC AGAGGTGGCA CCCAGGGGCC CGGGAACTCC TGCCACAACA GAATAAAGCA GCCTG

ATTG AAAAAAAAAAA

FIG. 5

Human SP5 cDNA #19

```
                               GAATTCGGAGCAC CTGCAGCAAG ATG GAT GTG GGC AGC AAA GAG GTC CTG ATG GAG AGC CCG CCG GAC TAC TCC GCA GCT
                                                        MET Asp Val Gly Ser Lys Glu Val Leu MET Glu Ser Pro Pro Asp Tyr Ser Ala Ala
                                                         1
                    100
CCC CGG GGC CGA TTT GGC ATT CCC TGC TGC CCA GTG CAC CTG AAA CGC CTT CTT ATC GTG GTG GTG GTG GTG GTC CTC ATC GTC GTG GTG
Pro Arg Gly Arg Phe Gly Ile Pro Cys Cys Pro Val His Leu Lys Arg Leu Leu Ile Val Val Val Val Val Val Leu Ile Val Val Val
                 24  25
                                       200
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
                                                             65
                                                   300
CAA CGC CTG GCC CTG AGT GAG CAC CTG GTT ACC ACT GCC ACC TTC TCC ATC GGC TCC ACT GGC CTC GTG GTG TAT GAC TAC CAG CAG CTG
Gln Arg Leu Ala Leu Ser Glu His Leu Val Thr Thr Ala Thr Phe Ser Ile Gly Ser Thr Gly Leu Val Val Tyr Asp Tyr Gln Gln Leu
 80                                                                                                              108
                                                                   400
CTG ATC GCC TAC AAG CCA GCC CCT GGC ACC TGC TGC TAC ATC ATG AAG ATA GCT CCA GAG AGC ATC CCC AGT CTT GAG GCT CTC ACT AGA
Leu Ile Ala Tyr Lys Pro Ala Pro Gly Thr Cys Cys Tyr Ile MET Lys Ile Ala Pro Glu Ser Ile Pro Ser Leu Glu Ala Leu Thr Arg
                                                                                                                 138
                                                                                     500
AAA GTC CAC AAC TTC CAG ATG GAA TGC TCT CTG CAG GCC AAG CCC GCA GTG CCT ACG TCT AAG CTG GGC CAG GCA GAG GGG CGA GAT GCA
Lys Val His Asn Phe Gln MET Glu Cys Ser Leu Gln Ala Lys Pro Ala Val Pro Thr Ser Lys Leu Gly Gln Ala Glu Gly Arg Asp Ala
                                                                                                 600
GGC TCA GCA CCC TCC GGA GGG GAC CCG GCC TTC CTG GGC ATG GCC GTG AGC ACC CTG TGT GGC GAG GTG CCG CTC TAC TAC ATC TAG GAC
Gly Ser Ala Pro Ser Gly Gly Asp Pro Ala Phe Leu Gly MET Ala Val Ser Thr Leu Cys Gly Glu Val Pro Leu Tyr Tyr Ile End
                                                                186                                        197
                                                                                        700
GCCTCCGGTG AGCAGGGTCA GTGGAAGCCC CAACGGGAAA GGAAACGCCC CGGGCAAAGG GTCTTTTGCA GCTTTTGCAG ACGGGCAAGA AGCTGCTTCT GCCCACACC

                                                                                 800
G CAGGGACAAG CCCTGGAGAA ATGGGAGCTT GGGGAGAGGA TGGGAGTGGG CAGAGGTGGC GCCCAGGGGC CCGGGAACTC CTGCCACAAC AGAATAAAGC AGCCTGA

TTG AAAAAAAAAAA
```

FIG. 6

```
GAA TTC GGC CTG ATG GAG AGC CCG CCG GAC TAC TCC GCA GCT CCC CGG      48
Glu Phe Gly Leu Met Glu Ser Pro Pro Asp Tyr Ser Ala Ala Pro Arg
 1               5                   10                  15
           Start
GGC CGA TTT GGC ATT CCC TGC TGC CCA GTG CAC CTG AAA CGC CTT CTT      96
Gly Arg Phe Gly Ile Pro Cys Cys Pro Val His Leu Lys Arg Leu Leu
             20                  25                  30

ATC GTG GTG GTG GTG GTG GTC CTC ATC GTC GTG GTG ATT GTG GGA GCC     144
Ile Val Val Val Val Val Val Leu Ile Val Val Val Ile Val Gly Ala
         35                  40                  45

CTG CTC ATG GGT CTC CAC ATG AGC CAG AAA CAC ACG GAG ATG GTT CTG     192
Leu Leu Met Gly Leu His Met Ser Gln Lys His Thr Glu Met Val Leu
     50                  55                  60

GAG ATG AGC ATT GGG GCG CCG GAA GCC CAG CAA CGC CTG GCC CTG AGT     240
Glu Met Ser Ile Gly Ala Pro Glu Ala Gln Gln Arg Leu Ala Leu Ser
 65                  70                  75                  80

GAG CAC CTG GTT ACC ACT GCC ACC TTC TCC ATC GGC TCC ACT GGC CTC     288
Glu His Leu Val Thr Thr Ala Thr Phe Ser Ile Gly Ser Thr Gly Leu
                 85                  90                  95

GTG GTG TAT GAC TAC CAG CAG CTG CTG ATC GCC TAC AAG CCA GCC CCT     336
Val Val Tyr Asp Tyr Gln Gln Leu Leu Ile Ala Tyr Lys Pro Ala Pro
            100                 105                 110

GGC ACC TGC TGC TAC ATC ATG AAG ATA GCT CCA GAG AGC ATC CCC AGT     384
Gly Thr Cys Cys Tyr Ile Met Lys Ile Ala Pro Glu Ser Ile Pro Ser
        115                 120                 125

CTT GAG GCT CTC AAT AGA AAA GTC CAC AAC TTC CAG ATG GAA TGC TCT     432
Leu Glu Ala Leu Asn Arg Lys Val His Asn Phe Gln Met Glu Cys Ser
    130                 135                 140

CTG CAG GCC AAG CCC GCA GTG CCT ACG TCT AAG CTG GGC CAG GCA GAG     480
Leu Gln Ala Lys Pro Ala Val Pro Thr Ser Lys Leu Gly Gln Ala Glu
145                 150                 155                 160

GGG CGA GAT GCA GGC TCA GCA CCC TCC GGA GGG GAC CCG GCC TTC CTG     528
Gly Arg Asp Ala Gly Ser Ala Pro Ser Gly Gly Asp Pro Ala Phe Leu
                165                 170                 175

GGC ATG GCC GTG AAC ACC CTG TGT GGC GAG GTG CCG CTC TAC TAC ATC     576
Gly Met Ala Val Asn Thr Leu Cys Gly Glu Val Pro Leu Tyr Tyr Ile
            180                 185                 190

TAG GAC GCT CCG GGT CAG TGG AAG CCC CAA CGG GAA AGG AAA CGC CCC     624
    Asp Ala Pro Gly Gln Trp Lys Pro Gln Arg Glu Arg Lys Arg Pro
            195                 200                 205

GGG CAA AGG GTC TTT TGC AGC TTT TGC AGA CGG GCA AGA AGC TGC TTC     672
Gly Gln Arg Val Phe Cys Ser Phe Cys Arg Arg Ala Arg Ser Cys Phe
        210                 215                 220

TGC CCA CAC CGC AGG GAC AAA CCC TGG AGA AAT GGG AGC TTG GGG AGA     720
Cys Pro His Arg Arg Asp Lys Pro Trp Arg Asn Gly Ser Leu Gly Arg
    225                 230                 235

GGA TGG GAG TGG GCA GAG GTG GCA CCC AGG GGC CCG GGA ACT CCT GCC     768
Gly Trp Glu Trp Ala Glu Val Ala Pro Arg Gly Pro Gly Thr Pro Ala
240                 245                 250                 255

ACA ACA GAA TAA AGC AGC CTG ATT GAA AAG CAA AAA AAA AAA AAA AAA     816
Thr Thr Glu  .  Ser Ser Leu Ile Glu Lys Gln Lys Lys Lys Lys Lys
                    260                 265                 270

ACC GAA TTC                                                         825
Thr Glu Phe
```

FIG. 13

CANINE SP5

N term

C term

```
        10         20         30         40         50         60
MDVGSKEVLI ESPPDYSAAP RGRLGIPCFP SSLKRLLIIV VVIVLVVVVI VGALLMGLHM

        70         80         90        100        110        120
SQKHTEMVLE MSMGGPEAQQ RLALQERVGT TATFSIGSTG IVVYDYQRLL IAYKPAPGTC

       130        140        150        160        170        180
CYIMKMTPEN IPSLEALTRK FQDFQVKPAV STSKLGQEEG HDAGSASPGD PLDFLGTTVS

       190
TLCGEVPLFY I.
```

FIG. 14

HUMAN SP5

N term

C term (by analogy with above)

```
        10         20         30         40         50         60
EFGLMESPPD YSAAPRGRFG IPCCPVHLKR LLIVVVVVVL IVVVIVGALL MGLHMSQKHT

        70         80         90        100        110        120
EMVLEMSIGA PEAQQRLALS EHLVTTATFS IGSTGLVVYD YQQLLIAYKP APGTCCYIMK

       130        140        150        160        170        180
IAPESIPSLE ALNRKVHNFQ MECSLQAKPA VPTSKLGQAE GRDAGSAPSG GDPAFLGMAV

       190
NTLCGEVPLY YI.
```

FIG. 15

HUMAN VS. DOG SP18

```
         10        20        30        40        50        60
MAESHLLQWLLLLLPTLCGPGTAAWTTSSLACAQGPEFWCQSLEQALQCRALGHCLQEVW
      ::::: :  : ::::::  ::  ::::::::::::::::::::::::::::
      LL-W-LLLLPTLCGLGAADWSAPSLACARGPAFWCQSLEQALQCRALGHCLQEVW

         70        80        90       100       110       120
GHVGADDLCQECEDIVHILNKMAKEAIFQDTMRKFLEQECNVLPLKLLMPQCNQVLDDYF
:  : ::::::: :::: :: :: :::::: :::::: : :: :::::: :::  : :
GNARADDLCQECQDIVRILTKMTKEAIFQDMVRKFLEHECDVLPLKLLTPQCHHMLGTYF

        130       140       150       160       170       180
PLVIDYFQNQIDSNGICMHLGLCKSRQPEPEQEPGMSDPLPKPLRDPLPDPLLDKLVLPV
 :: ::::.: :: :: :::::::  :::::::::::::            ::::  :
PVVVDYFQSQINPKIICKHLGLCKPGLPEPEQESELSDPL------------LDKLILPE

                     H2N-
        190       200    210       220       230       240
LPGALQARPGPHTQDLSEQQFPIPLPYCWLCRALIKRIQAMIPKGALRVAVAQVCRVVPL
::::::  : ::::::::::.::::::::::: :::::::::: : : : ::::::::
LPGALQVT-GPHTQDLSEQQLPIPLPYCWLCRTLIKRIQAMIPKGVLAVTVGQVCHVVPL

                                  COO-
        250       260       270    280      290
VAGGICQCLAERYSVILLDTLLGRMLPQLVCRLVLRCSMDDSAGPRSPTG--EWLPRDSE
 :::::::: ::::.:::: :::::::::: : ::::  :::::: :   :  ::  :
VVGGICQCLGERYTVLLLDALLGRMLPQLVCGLVLRCSHEDSAGPALASLPSEWSPQESK

        310       320       330       340       350
CHLCMSVTTQAGNSSEQAIPQAMLQACVGSWLDREKCKQFVEQHTPQLLTLVPRGWDAHT
:.:::.::::::: :::: ::: ::::::::::: : ::::::. : :::: :: :::
CQLCMFVTTQAGNHSEQATPQAIRQACLSSWLDRQKCEQFVEQHMPRLQTLASGGRDAHT

        370       380
TCQALGVCGTMSSPLQCIHSPDL.
::::::   :: ::::::: :
TCQALGACRTTFSPLQCIHIPHF.
```

FIG. 16

RECOMBINANT ALVEOLAR SURFACTANT PROTEIN

This application is a continuation of application Ser. No. 07/639,250, filed Jan. 7, 1991, now abandoned, which is a continuation of application Ser. No. 07/117,099, filed Nov. 4, 1987, now abandoned, which is a continuation-in-part of application Ser. No. 07/008,453, filed Jan. 29, 1987, now abandoned, which is a continuation-in-part of application Ser. No. 06/857,715, filed Apr. 30, 1986, now U.S. Pat. No. 4,933,280, which is a continuation-in-part of application Ser. No. 06/808,843, filed Dec. 13, 1985, now U.S. Pat. No. 4,912,038, which is a continuation-in-part of application Ser. No. 06/680,358, filed Dec. 11, 1984, now U.S. Pat. No. 4,659,805.

TECHNICAL FIELD

The invention relates to the field of recombinant protein production. More specifically it relates to the production of alveolar surfactant protein (ASP) which is useful in the management of certain respiratory diseases.

BACKGROUND ART

The human lung is composed of a large number of small sacs or alveoli in which gases are exchanged between the blood and the air spaces of the lung. In healthy individuals, this exchange is mediated by the presence of a protein containing surfactant complex which is synthesized in the microsomal membranes of type II alveolar cells. In the absence of adequate levels of this complex, a lung cannot properly function—i.e., the alveoli collapse during exhalation, and cannot be subsequently re-inflated by inhaling. Thus, the untreated inability to synthesize this complex may result in death or in severe physical damage.

The best documented instance of inadequate surfactant complex levels occurs in premature infants and infants born after complicated pregnancies, and is widely known as respiratory distress syndrome (RDS). A widely publicized form of this syndrome has been designated hyaline membrane disease, or idiopathic RDS. RDS is currently the leading cause of infant mortality and morbidity in the United States and in other developed countries, and substantial efforts have been directed to diagnosis and treatment. Current treatment has focused on mechanical (pressure) ventilation which, at best, is an invasive stop-gap measure that often results in damage to the lung and other deleterious side effects, including complications such as bronchopulmonary dysplasia, interstitial emphysema and pneumothorax. Mental retardation has also resulted on occasion when this treatment was used (Hallman, M., et al, *Pediatric Clinics of North America* (1982) 29:1057–1075).

Limited attempts have been made to treat the syndrome by surfactant substitution. This would be a method of choice, as, in general, only one administration is required, and the potential for damage is reduced. For example, Fujiwara, et al, *Lancet* (1980) 1:55-used a protein-depleted surfactant preparation derived from bovine lungs, while Hallman, M., et al, *Pediatrics* (1983) 71:473–482 used a surfactant isolated from human amniotic fluid to treat a limited number of infants with some success. U.S. Pat. No. 4,312,860 to Clements discloses an artificial surfactant which contains no protein and is said to be useful in this approach although no data are shown. In short, surfactant substitution has not been widely used clinically.

The preferred surfactant substitute would be the lung surfactant complex itself. This complex is composed of apoprotein, two phospholipids (dipalmitoyl phosphocholine (DPPC) and phosphatidyl-glycerol (PG)) which are present in major amount, several lipid components present in only very minor amount, and calcium ions. The apoprotein contains proteins having molecular weights of the order of 32,000 daltons and very hydrophobic proteins of the order of about 10,000 daltons (King, R. J. et al, *Am J Physiol* (1973) 224:788–795). The 32,000 dalton protein is glycosylated and contains hydroxyproline.

A major reason for the limited progress in surfactant replacement therapy has been the lack of availability of the protein portion of the complex. Replacement therapies have focused on attempts to use the lipid components alone, and it appears that the performance of such treatment can be markedly improved by addition of the apoprotein (Hallman, M., et al, *Pediatric Clinics of North America* (1982) (supra)). At present, however, these proteins are available only from normal adult human lung, and from amniotic fluid. Even efficient isolation procedures would not provide an adequate supply. Thus, it would be desirable to have available a method for producing practical quantities of apoprotein for use alone or in conjunction with the saturated phospholipid portion of the complex.

Related PCT patent application W086/03408 describes the recombinant production of the human ASP protein of about 32 kd, the retrieval of DNA sequences encoding various canine ASP proteins and the retrieval of a single representative of the human ASP protein group of about 10 kd molecular weight. It is now clear that efficient production of the "10K" group is required for use in adequate therapy.

DISCLOSURE OF INVENTION

The invention provides a means for obtaining the apoprotein portion of the lung surfactant complex in quantity and under conditions which permit optimization of its features. The remaining components of the complex, dipalmitoyl phosphocholine and phosphatidylglycerol, along with calcium ions are already readily available. The availability of required quantities of manipulable apoprotein both makes possible research efforts to optimize the form of complex useable in therapy, and opens the possibility for routine replacement therapy of respiratory distress syndrome.

Thus, in one aspect, the invention relates to recombinantly produced mammalian alveolar surfactant protein (ASP). These proteins are mixtures of relatively high molecular weight, relatively water soluble proteins of about 32 kd (32K ASP) and of lower molecular weight, hydrophobic proteins of about 10–20 kd (10K ASP). Both proteins encourage formation of surface tension lowering films when complexed with phospholipid in the presence of calcium ion. The invention further relates to DNA sequences encoding mammalian ASP, including human and canine 32K and 10K ASP, to expression vectors suitable for production of these proteins, to recombinant host cells transformed with these vectors, and to methods of producing the recombinant ASPs and their precursors. In other aspects the invention relates to pharmaceutical compositions containing human ASP and to methods of treating RDS using them.

In still other aspects, the invention relates to improved methods to isolate the 32K ASP proteins, and to purified bovine 10K forms.

The invention further relates to synthetic peptides based on the 5 kd protein sequence of the 10K mixture (previously identified as a "6 kd" protein in the parent application hereto).

BREIF DESCRIPTION OF THE DRAWINGS

FIGS. 1-1 and 1-2 show the DNA sequence (along with the deduced amino acid sequence) determined for cDNA encoding a canine 18 kd ASP protein from overlapping cDNA clones, showing the overlapping pD10k-1 and pD10k-4 clones identified.

FIGS. 2-1 and 2-2 show cDNA sequence and deduced amino acid sequence for "cDNA No. 3" encoding human 18 kd ASP protein.

FIGS. 3-1 and 3-2 show the DNA sequence and deduced amino acid sequence of the exon portions of the genomi-ϵ DNA encoding human 18 kd protein.

FIG. 4 shows the sequence of oligonucleotide probes used to isolate the cDNA encoding human 5 kd/8 kd protein.

FIG. 5 shows the DNA and deduced amino acid sequence of cDNA No. 18 encoding human 5 kd protein.

FIG. 6 shows an analogous cDNA No. 19 encoding human 5 kd protein.

FIG. 13 is the DNA sequence determined for a cDNA encoding the 5 kd protein in the human 10K ASP mixture.

FIG. 14 is the amino acid sequence of the canine 5 kd protein, with the N-terminus and C-terminus as marked.

FIG. 15 is the amino acid sequence of the human 5 kd protein, with the N-terminus and C-terminus as marked.

FIG. 16 illustrates the correlation between the human and canine 18 kd proteins in the 10K ASP mixture.

MODES OF CARRYING OUT THE INVENTION

A. Definitions

Figure 7A:
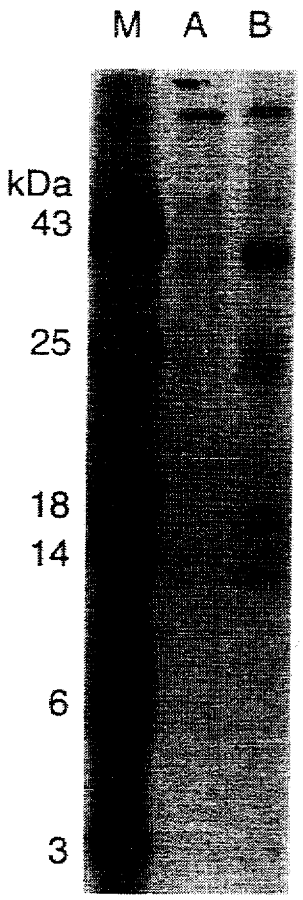
FIGS. 7A and 7B are results of SDS-PAGE without and with endo F enzyme treatment of $^{35}S$ labeled proteins produced in CHO cells transfected with vector encoding human 18 kd protein.

As used herein, "alveolar surfactant protein (ASP)" refers to apoprotein associated with the lung surfactant complex and having ASP activity as defined hereinbelow. The ASP of all species examined appears to comprise one or more components of relatively high molecular weight (of the order of 32 kd) designated herein "32K ASP" and one or more quite hydrophobic components of relatively low molecular weight (of the order of 5–20 kd) designated herein "10K ASP". (King, R. J., et al, *J Appl Physiol* (1977) 42:483–491; Phizackerley, P. J. R., *Biochem J* (1979) 183:731–736.)

The 32K proteins for all species appear to be derived from a single primary amino acid sequence, in each case (although there is evidence that the protein is encoded by multiple genes encoding proteins with minor variations in sequence). The multiple components, found under some conditions, however, of differing molecular weights, are due to variations in glycosylation patterns. Related application W086/03408 disclose the complete amino acid sequence for the human and canine 32K ASP proteins which show a high degree of homology. This set of high molecular weight, relatively hydrophilic proteins forms the subject matter of said application, and the 32K ASP derived from alternate mammalian species is expected to exhibit a high degree of homology with the canine and human sequences presented.

The low molecular weight "10K" proteins are relatively hydrophobic and also appear to be mixtures of several proteins of varying molecular weight. Both the human and canine proteins exhibit unreduced molecular weights of 18 kd, 8 kd, and 5 kd. The 8 kd and 5 kd proteins appear to be identical in N-terminal sequence and are presumably derived from the same message but contain variations in C-terminal processing, or, more likely, the 8 kd protein may be a dimer of the 5 kd protein. The 18 kd protein, which shows a molecular weight of 10 kd under reducing conditions, on the other hand, has a clearly different amino acid sequence. However, the 18 kd, 8 kd and 5 kd proteins of the mammalian species concerned herein, all appear to function equivalently in vivo. The invention herein primarily concerns this 10K group. Related application W086/03408 discloses the complete cDNA and deduced amino acid sequence for the 18 kd canine protein, but only a partial DNA sequence for the human counterpart. Only a short N-terminal amino acid sequence for the 8 kd/5 kd canine protein was disclosed; the appropriate cDNA has now been recovered for the human protein and the complete sequence of both representative 10K proteins made part of the art. Because the 10K mixture seems to show products of only two DNA sequences, although variations in posttranslational processing can result in multiple molecular weights, the designations SP-18 and SP-5 have been adopted for those two types of proteins and genes.

FIG. 1 herein corresponds to FIG. 2 of W086/03408 and shows the complete cDNA sequence for the precursor protein to the mature canine SP-18 protein beginning at leucine shown at position 1 and ending at phenylalanine at position 183 (the mature canine SP-18 protein itself begins at that leucine and ends at His-79 as illustrated in FIG. 1). The corresponding sequence for the human SP-18 protein is shown in FIGS. 2 and 3, sequences which differ only slightly in amino acid sequence as described hereinbelow. The start of the mature human protein is the phenylalanine residue at position 201 of FIG. 2 ending with the arginine at position 276. The cDNA thus putatively encodes a 181 amino acid protein for the human. Both the human and dog proteins are, however, thought to be processed to shorter sequences by deletion of a portion of the carboxy-terminal sequence. For the human protein, as noted, this is thought to occur so that the secreted protein terminates with the methionine shown at position 279 in FIG. 2. Such processing would result in a protein of molecular weight about 10K seen in reduced electrophoresis gels of isolated mature protein.

The cDNA and deduced amino acid sequences for two analogous forms of human SP-5 protein are shown in FIGS. 5 and 6. Again, although the cDNA, starting at the putative N-terminus of the mature protein encodes 173 or 174 amino acids, variations in C-terminal processing or dimerization results in isolated proteins of 5 kd or 8 kd.

In summary, the 10K group of lower molecular weight proteins appears to derive from DNAs encoding two different species designated herein SP-18 and SP-5. The SP-18 encoded species are so named because they encode a putative mature protein of approximately 18 kd; however, posttranslational processing appears to result in proteins and possibly dimers of lower molecular weight. (Coincidentally, the approximately 20 kd protein dimer resulting from the processed protein, under reducing conditions, runs in gels at the position expected for a 10 kd protein.) Similarly, the SP-5 cDNA encodes a protein of putative molecular weight of approximately 19 kd. However, again, this molecular weight protein is not found in extracts, and the encoded amino acid sequence is evidently processed and/or dimerized to the 5 kd and 8 kd proteins obtained.

The recombinant ASP proteins of the invention have amino acid sequences corresponding to those of the native proteins. It is understood that limited modifications may, however, be made without destroying activity, and that only a portion of the entire primary structure may be required. For example, the human ASP 32K recombinant protein of the invention has an amino acid sequence substantially similar to that shown in FIG. 3, but minor modifications of this sequence which do not destroy activity also fall within the definition of 32K human ASP and within definition of the protein claimed as such, as further set forth below. Also included within the definition are fragments of the entire sequence of FIG. 3 which retain activity.

As is the case for all proteins, the ASP proteins can occur in neutral form or in the form of basic or acid addition salts depending on its mode of preparation, or, if in solution, upon its environment. It is well understood that proteins in general, and, therefore, any ASP, in particular, may be found in the form of its acid addition salts involving the free amino groups, or basic salts formed with free carboxyls. Pharmaceutically acceptable salts may, indeed, enhance the functionality of the protein. Suitable pharmaceutically acceptable acid addition salts include those formed from inorganic acids such as, for example, hydrochloric or sulfuric acids, or from organic acids such as acetic or glycolic acid. Pharmaceutically acceptable bases include the alkali hydroxides such as potassium or sodium hydroxides, or such organic bases as piperidine, glucosamine, trimethylamine, choline, or caffeine. In addition, the protein may be modified by combination with other biological materials such as lipids and saccharides, or by side chain modification, such as acetylation of amino groups, phosphorylation of hydroxyl side chains, or oxidation of sulfhydryl groups or other modification of the encoded primary sequence. Indeed, in its native form, the 32K ASP is a glycosylated protein, and certain of the encoded proline residues have been converted to hydroxyproline. It is also found in association with the phospholipids DPPC and PG. Included within the definition of any ASP herein are glycosylated and unglycosylated forms, hydroxylated and non-hydroxylated forms, the apoprotein alone, or in association with lipids, and, in short, any composition of an amino acid sequence substantially similar to that of the native sequences which retains its ability to facilitate the exchange of gases between the blood and lung air spaces and to permit re-inflation of the alveoli.

It is further understood that minor modifications of primary amino acid sequence may result in proteins which have substantially equivalent or enhanced activity as compared to the native sequences. These modifications may be deliberate, as through site-directed mutagenesis, or may be accidental, such as through mutation of hosts which are ASP producing organisms. All of these modifications are included as long as the ASP activity is retained.

"ASP activity" for a protein is defined as the ability, when combined with lipids either alone or in combination with other proteins, to exhibit activity in the in vivo assay of Robertson, B. *Lung* (1980) 158:57–68. In this assay, the sample to be assessed is administered through an endotracheal tube to fetal rabbits or lambs delivered prematurely by Caesarian section. (These "preemies" lack their own ASP, and are supported on a ventilator.) Measurements of lung compliance, blood gases and ventilator pressure provide indices of activity. Preliminary assessment of activity may also be made by an in vitro assay, for example that of King, R. J., et al, *Am J Physiol* (1972) 223:715–726, or that illustrated below of Hawgood, et al, which utilizes a straightforward measurement of surface tension at a air-water interface when the protein is mixed with a phospholipid vesicle preparation. The 10K and 32K ASP proteins described herein show ASP activity in combination as well as independently. Although it had previously been believed that the 10K protein displayed ASP activity only when acting in concert with the 32K family, the inventors of the present invention have now demonstrated that the 10K protein alone displays significant ASP activity.

"Operably linked" refers to a juxtaposition wherein the components are configured so as to perform their usual function. Thus, control sequences operably linked to coding sequences are capable of effecting the expression of the coding sequence.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Cells" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

B. GENERAL DESCRIPTION

The methods illustrated below to obtain DNA sequences encoding ASP are merely for purposes of illustration and are typical of those that might be used. However, other procedures may also be employed, as is understood in the art.

B.1. The Nature of the Surfactant Complex

The alveolar surface of lung has been studied extensively by a number of techniques, and by a number of groups. It appears that the basement membrane of the alveolus is composed of type I and type II alveolar cells, of which the type II cells comprise approximately 3% of the surface. The type II cells are responsible for the exocrine secretion of materials into a lining fluid layer covering the basement membrane, which materials decrease the surface tension between the liquid of the lining and the gas phase of the contained volume. The fluid layer, then, is comprised of water derived from the blood plasma of the alveolar capillaries, and the surfactant secretions of the type II cells.

The type II cells, themselves, contain 60–100 pg of protein and about 1 pg of lipid phosphorus per cell where the ratio between tyepe II cell DPPC and PG phosphorus is about 8 to 1. Studies of the apoprotein components have been based on pulmonary lavage from various species, and have been shown to comprise two major proteins, as discussed above, of approximate molecular weights 10–20 kd and of 32 kd (Kikkawa, Y., et, al, *Laboratory Investigation* (1983) 49:122–139.) It is not clear whether the apoproteins are bound to the phospholipid component (King R. J., et al, *Am Rev Respir Dis* (1974) 110:273) or are not (Shelly, S. A., et al *J Lipid Res* (1975) 16:224).

It has been shown that the higher molecular weight protein obtained by pulmonary lavage of dogs, and separated by gel electrophoresis is composed of 3 major components of molecular weight 29,000, 32,000, and 36,000 daltons. (See, U.S. Ser. No. 665,018, filed 26 October 1984, assigned to the same assignee, and incorporated herein by reference.) The 32,000 dalton protein was used to obtain sequence data, as set forth below; however, all 3 of these proteins have identical N-terminal sequences, and there is evidence that they differ only in degree of glycosylation. Digestion of the 36 kd and 32 kd bands with endoglycosidase F, which removes carbohydrate side chains, results in products which co-migrate with the 29 kd component. The mobility of the 29 kd component is unaffected by this treatment. It has also been shown that the 32 kd fraction aggregates into dimers and trimers.

The smaller molecular weight proteins are extracted with more difficulty, but these, too, appear to be mixtures (Phizackerley et., supra; description below). For both the dog and human proteins, which have been studied with respect to their encoding DNA, and with respect to bovine lavage, studied at the protein level, the lower molecular weight protein mixtures appear to contain two types of amino acid sequence, designated herein SP-18 and SP-5. The SP-18 sequences are encoded by cDNA corresponding to a molecular weight primary sequence of approximately 44 kd; approximately 381 amino acids. However, the products appear to be processed in vivo to shorter proteins. The SP-5 DNA encodes a precursor protein of approximately 197 amino acids, but this protein, too, is processed to substantially smaller proteins apparently of approximately 5 kd and 8 kd. The processing referred to above seems to comprise deletion of sequences from the N- and the C-terminus of the proteins produced, and/or dimerization.

B.2. Cloning of Coding Sequences for Canine and Human ASP Proteins

The entire canine and human ASP 32K protein encoding sequences have been cloned and expressed as set forth in W086/03408. DNA sequences encoding several of the lower molecular weight proteins from both human and canine sources have also been obtained and expressed.

The canine lung cDNA library was probed with two synthetic oligomer mixtures designed to correspond to the N-terminal amino acid sequence of an 18 kd (on unreduced gels) canine protein, and clones hybridizing to both probes were recovered and sequenced; this provided the information set forth in FIG. 1 herein. One of these clones, which contained canine ASP encoding sequence, was used to probe a cDNA library prepared in bacteriophage λgt10 from mRNA isolated from adult human lung to obtain a human SP-18; which was, in turn, used to probe a human genomic library. The complete sequence(s) for human SP-18 encoded by the cDNA and by the genomic clone are disclosed. Probes designed corresponding to the N-terminal amino acid sequence of a 5 kd canine protein were then used to obtain SP-5 cDNA from the λgt10 lung library. Variants of this sequence are also disclosed.

B.3. Expression of ASP

As the nucleotide sequences encoding the various human and canine ASP are now available, these may be expressed in a variety of systems as set forth in ¶C. If procaryotic systems are used, an intronless coding sequence should be used, along with suitable control sequences. The cDNA clones for any of the above ASP proteins may be excised with suitable restriction enzymes and ligated into procaryotic vectors for such expression. For procaryotic expression of ASP genomic DNA, the DNA should be modified to remove the introns, either by site-directed mutagenesis, or by retrieving corresponding portions of cDNA and substituting them for the intron-containing genomic sequences. The intronless coding DNA is then ligated into expression vectors for procaryotic expression. Several illustrative expression systems are set forth below.

As exemplified below, ASP encoding sequences may also be used directly in an expression system capable of processing the introns, usually a mammalian host cell culture. To effect such expression, the genomic sequences can be ligated downstream from a controllable mammalian promoter which regulates the expression of these sequences in CHO cells.

In addition to recombinant production, proteins of the invention of sufficiently short length, such as the 5 kd protein, may be prepared by protein synthesis methods.

B.4. Protein Recovery

The ASP protein may be produced either as a mature protein or a fusion protein, or may be produced along with a signal sequence in cells capable of processing this sequence for secretion. It is advantageous to obtain secretion of the protein, as this minimizes the difficulties in purification; thus it is preferred to express the human ASP gene which includes the codons for native signal sequence in cells capable of appropriate processing. It has been shown that cultured mammalian cells are able to cleave and process heterologous mammalian proteins containing signal sequences, and to secrete them into the medium (McCormick, F., et al, *Mol Cell Biol* (1984) 4:166).

When secreted into the medium, the ASP protein is recovered using standard protein purification techniques. The purification process is simplified, because relatively few proteins are secreted into the medium, and the majority of the secreted protein will, therefore, already be ASP. However, while the procedures are more laborious, it is within the means known in the art to purify this protein from sonicates or lysates of cells in which it is produced intracellularly in fused or mature form.

B.5. Improved Method for 32K ASP Purification

Disclosed herein is a particularly advantageous process for the purification of the 32K proteins produced either natively or recombinantly which takes advantage of the similarity of certain domains of the primary sequence to the carbohydrate binding moieties of lectins.

Accordingly, one aspect of the invention herein is a process for purification of the 32K ASP proteins which comprises subjecting a mixture containing such proteins to affinity chromatography in which the moiety responsible for the affinity is a carbohydrate, especially mannose or a carbohydrate-bound protein. As illustrated below, e.g. mannose itself directly coupled to a suitable support such as agarose or Sepharose (a trademark of Pharmacia, Inc., Piscatawy, New Jersey) or other commonly used chromatographic solid supports, or glycoproteins containing high levels of mannose may be employed. While mannose is most preferred, other functional affinity partner carbohydrates include fructose and N-acetyl glucosamine. The variation of design in chromatographic support for a particular affinity group is well understood by practitioners of the art, and any configuration which provides the carbohydrate as the available adsorbent is suitable.

The binding advantageously takes place in the presence of low concentrations of calcium ion, and elution is advantageously conducted by removal of calcium ion using, for example, EDTA. However, elution may also be effected by a substance in the elution solvent which competes with the affinity column for binding to ASP, such as increasing concentrations of mannose or galactose. Elution can also be performed by supplying reducing agents, as reduction of disulfide bonds releases the binding, as do high and low pH. While low pH may cause denaturation, elution in borate buffer at about pH 10 is effective.

B.6. Assay for ASP Activity

In vitro methods have been devised to assess the ability of ASP proteins to function by reducing surface tension (synonymous with increasing surface pressure) to generate a film on an aqueous/air interface. Studies using these methods have been performed on the isolated native 10K canine ASP. (Benson, B. J., et al *Prog Resp Res* (1984) 18:83–92; Hawgood, S., et al, *Biochemistry* (1985) 24:184–190.)

Tanaka, Y, et al, *Chem Pharm Bull* (1983) 31:4100–4109 disclose that a 35 kd protein obtained from bovine lung enhanced the surface spreading of DPPC; Suzuki, Y., *J Lipid Res* (1982) 23:62–69; Suzuki, Y., et al, *Prog Resp Res* (1984) 18:93–100 showed that a 15 kd protein from pig lung enhanced the surface spreading of the lipid-protein complex from the same source.

Since the function of the surfactant complex in vivo is to create a film at the air/aqueous interface in order to reduce surface tension, the ability of ASP proteins to enhance the formation of the film created by the spread of lipid or lipoprotein at such a surface in an in vitro model is clearly relevant to its utility.

An in vivo model, described in the examples, may also be employed.

B. 7. Administration and Use

The purified proteins can be used alone and in combination in pharmaceutical compositions appropriate for administration for the treatment of respiratory distress syndrome in infants or adults. The compositions and protein products of the invention are also useful in treating related respiratory diseases such as pneumonia and bronchitis. The complex contains about 50% to almost 100% (wt/wt) lipid and 50% to less than 1% ASP; preferably ASP is 5%–20% of the complex. The lipid portion is preferably 80%–90% (wt/wt) DPPC with the remainder unsaturated phosphatidyl choline, phosphatidyl glycerol, triacylglycerols, palmitic acid or mixtures thereof. The complex is reassembled by mixing a solution of ASP with a suspension of lipid liposomes, or by mixing the lipid protein solutions directly in the presence of detergent or an organic solvent. The detergent or solvent may then be removed by dialysis or evaporation.

While it is possible to utilize the natural lipid component from lung lavage in reconstructing the complex, and to supplement it with appropriate amounts of ASP proteins, the use of synthetic lipids is clearly preferred. First, there is the matter of adequate supply, which is self-evident. Second, purity of preparation and freedom from contamination by foreign proteins, including infectious proteins, which may reside in the lungs from which the natural lipids are isolated, are assured only in the synthetic preparations. Of course, reconstitution of an effective complex is more difficult when synthetic components are used.

As noted above, it had been previously believed that the 10K ASP mixture served primarily to enhance the activity of the 32K mixture; however, it has now be established by the inventors herein that a preferred composition comprises either a complex with the 10K protein alone, the SP-5 or SP-18 protein alone, a complex of the 10K and 32K mixtures, or a complex of an SP-18 or SP-5 protein and the 32K mixture. In the latter case, a preferred protein ratio—i.e., 32K:10K or 32K:SP-18 or 32K:SP-5—is typically in the range of 3:1 to 200:1, preferably about 10:1 to 5:1. The 32K protein may be added directly to an aqueous suspension of phospholipid vesicles in an aqueous solution. Because it is so hydrophobic, the 10K protein is added to the lipids in an organic solvent, such as chloroform, the solvents evaporated, and the vesicles re-formed by hydration.

The addition of the 32K protein to the 10K type for the administration of the surfactant complex appears to have a synergistic effect—i.e., the combination of 32K and 10K type proteins exerts the desired activity at protein concentrations lower than those required for the 10K protein alone. Accordingly, in a preferred method of the invention, the surfactant complex administered will contain an effective amount of the 10K mixture, or of the individual SP-5 or SP-18 proteins in admixture with the 32K ASP. Particularly preferred compositions contain the ratios of 32K:10K type protein as set forth above, along with a suitable amount of lipid component, typically in the range of 50% to almost 100% of the composition.

The compositions containing the complex are preferably those suitable for endotracheal administration, i.e., generally as a liquid suspension, as a dry powder "dust" or as an aerosol. For direct endotracheal administration, the complex is suspended in a liquid with suitable excipients such as, for example, water, saline, dextrose, or glycerol and the like. The compositions may also contain small amounts of nontoxic auxiliary substances such as pH buffering agents, for example, sodium acetate or phosphate. To prepare the "dust", the complex, optionally admixed as above, is lyophilized, and recovered as a dry powder.

If to be used in aerosol administration, the complex is supplied in finely divided form along with an additional surfactant and propellant. Typical surfactants which may be administered are fatty acids and esters, however, it is preferred, in the present case, to utilize the other components of the surfactant complex, DPPC and PG. Useful propellants are typically gases at ambient conditions, and are condensed under pressure. Lower alkanes and fluorinated alkanes, such as Freon, may be used. The aerosol is packaged in a container equipped with a suitable valve so that the ingredients may be maintained under pressure until released.

The surfactant complex is administered, as appropriate to the dosage form, by endotracheal tube, by aerosol administration, or by nebulization of the suspension or dust into the inspired gas. Amounts of complex between about 0.1 mg and 200 mg, preferably 50–60 mg/kg body weight, are administered in one dose. For use in newly born infants, one administration is generally sufficient. For adults, sufficient reconstituted complex is administered to replace demonstrated levels of deficiency (Hallman, M., et al, *J Clinical Investigation* (1982) 70:673–682).

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. These methods are set forth with particularity in W086/03408.

As set forth in that application, expression may be achieved in a variety of host systems including, in particular, mammalian and bacterial systems, as well as yeast based systems. In addition, other cell systems have become available in the art, such as the baculovirus vectors used to express protein encoding genes in insect cells. The expression systems set forth below are illustrative, and it is understood by those in the art that a variety of expression systems can be used.

D. EXAMPLES

D.1. Isolation of Mammalian ASP Proteins

Canine, human and bovine ASP proteins were obtained in purified form.

D.1.a. Isolation of the Canine Surfactant Complex

Lung surfactant complex was prepared from canine lungs obtained from exsanguinated canines. All procedures, including the lavage, were performed at 4° C. and the isolated material was stored at −15° C.

The lungs were degassed and lavaged 3 times with one liter per lavage of 5 mM Tris-HCl, 100 mM NaCl, pH 7.4 buffer. The $Ca^{+2}$ concentration of this buffer was less than $5\times10^{-6}$M (Radiometer F2112 Ca; Radiometer A/S, Copenhagen, Denmark). The pooled lung washings were spun at $150\times g_{av}$ for 15 min (Sorval RC2-B) to remove cellular material. The supernatant was then spun at $20{,}000\times g_{av}$ for 15 hr (Beckman L3-40) using a type 15 rotor (Beckman Instruments), and the resulting pellet was dispersed in buffer containing 1.64M sodium bromide. After equilibration for 1 hr, the suspension was spun at $100{,}000\times g_{av}$ for 4 hr (Beckman L5-50B) in a SW28 rotor (Beckman Instruments). The pellicle was resuspended in buffer and spun at $100{,}000\times g_{av}$ for 1 hr (Beckman L5-50B). This pellet containing the complex was resuspended in double distilled water.

Pellet resuspended in water at a concentration of 10–15 mg phospholipid/ml was injected into a 50-fold volume excess of n-butanol (Sigrist, H., et al., *Biochem Biophys Res Commun* (1977) 74:178–184) and was stirred at room temperature for 1 hr. After centrifugation at $10{,}000\times g_{av}$ for 20 min (Sorval RC2-B), the pellet, which contains the 32K ASP is recovered for further purification as described below. The supernatant, which is a single phase, contains the lipids and the lower molecular weight proteins. To obtain the lipids, the supernatant was dried under vacuum at 40° C. and the lipids were extracted (Folch, J., et al, *J Biol Chem* (1957) 226:497–509).

To obtain the hydrophobic protein, the supernatant was subjected to rotary evaporation to remove the butanol, and further dried by addition of ethanol followed by rotary evaporation. The dried residue was suspended in redistilled chloroform containing 0.1N HCl, and insoluble material removed by centrifugation.

The resulting solution was chromatographed over an LH-20 column (Pharmacia) and developed in chloroform. (LH-20 is the hydroxpropyl derivative of Sephadex G-25; it is a hydrophobic gel which is inert to organic solvents.) The proteins are excluded; lipids/phospholipids elute from the included volume.

Protein was recovered from the void volume fractions by evaporation of the chloroform under nitrogen, and then subjected to sizing on polyacrylamide gels. When run under non-reducing conditions, bands of approximately 18 kd (previously identified in the parent applications hereto as 16.5 kd), 10 kd, 8 kd (previously identified in the parent applications hereto as 12 kd), and 5 kd (previously identified in the parent applications hereto as 6 kd) were obtained; under reducing conditions, a single broad band of 5–12 kd was found.

The 18 kd, 8 kd, and 5 kd bands from the non-reduced gels were subjected to N-terminal analysis by Edman degradation, to give the following sequences:

For 18 kd:

Phe—Pro—Ile—Pro—Leu—Pro—Tyr—Cys—Trp—Leu—Cys—
Arg—Thr—Lue—Ile—Lys—Arg—Ile—Gln—Ala—Met—Ile—
Pro—Lys—Gly—Gly—Val—Leu—Ala—Val—Thr—?—Gly—
Gln—

For 8 kd:

Ile—Pro—Cys—Phe—Pro—Ser—Ser—Leu—Leu—Lys—Arg—
Leu—Leu—Ile

For 5 kd:

Ile—Pro—Cys—Phe—Pro—Ser—Ser—Leu—Lys—Arg—Leu—

-continued

Leu—Ile

The 5-12 kd band thus represents a mixture of the 18 kd, 8 kd and 5 kd proteins, designated herein as the "10K" mixture of proteins.

The precipitate from the n-butanol extraction above was used to obtain the purified 32K apoprotein as described in WO86/03408 (supra).

D.1.b. Isolation of Human ASP

Human 32K and lower molecular weight ASP was prepared following the procedure described in the published WO86/03408.

The isolated low molecular weight hydrophobic proteins show bands corresponding to 18 kd, 8 kd and 5 kd when subjected to polyacrylamide gel electrophoresis under non-reducing conditions. Under reducing conditions, a single broad band corresponding to 5-12 kd is obtained. The molecular weights of these bands are slightly different from those reported in the published application.

D.1.c. Isolation of Bovine ASP

The 10K bovine ASP containing 5 kd and 18 kd proteins was isolated from the lavage fluid of bovine lungs, in a method similar to that used for canine ASP.

Excised bovine lungs were filled with Tris-buffered saline, and the fluid removed from the lungs by vacuum. The lavage was centrifuged at 200×g for 10 minutes and the supernatant recovered and centrifuged at 8-9000×g for 20 minutes. The (surfactant) pellet was then suspended in 0.8M sucrose, which has a density greater than the buoyant density of the surfactant, and centrifuged at about 100,000×g for three hours. The floating surfactant was then suspended in water and sedimented at about 9-10,000×g for 20 minutes to remove the sucrose.

The phospholipid-rich surfactant was first extracted with 98% n-butanol, into which up to 2% aqueous surfactant (by volume) was added. This one-phase extraction allows solubilization of the 5 kd and 18 kd proteins and lipids while causing precipitation of the other proteins, which were removed by centrifuging at 9-10,000 gx. The butanol solution was then chromatographed over an LH-20 gel permeation column (Pharmacia) to separate the lipids from the 5 kd and 18 kd proteins. The desired protein peak was then rechromatographed over LH-60 which separates the 18 kd from the 5 kd protein. Both columns are run using chloroform:methanol (2:1, v/v) containing 0.5% 0.1N HC1.

The purified 5 kd and/or 18 kd proteins, either alone or in combination (1:1), were mixed in various weight ratios with synthetic phospholipids to obtain an effective surfactant.

D.2. cDNA encoding Canine 10K ASP Proteins

Messenger RNA extracted from adult canine lung tissue was used to prepare a DNA library using GC tailing in pBR322 as described in W086/03408 (supra).

The SP-18 Protein: Two oligomeric probes were synthesized corresponding to the NOterminal sequence of the 18 kd protein using mammalian codon preference tables for codon choice. Probe 1198 was a 36-mer of the sequence 5'-GGTCACAGCCAGGCCCTTGG-GGATCATGGCCTGGAT-3'; probe 1199 was a 45-mer of the sequence 5'-CTTGATCAGGGTTCT-GCACAGCCAGCAGTAGGGCAGGG-GGATGGG-3'. Both were labeled with $^{32}P$ by kinasing.

For hybridization, filters were baked at 80° C. for two hours under vacuum and then washed for 4 hr at 68° C. with shaking in a large volume of 3×SSC containing 0.1% SDS. The filters were prehybridized for several hours at 42° C. in 6×SSC, 5×Denhardt's, 20% formamide, 0.1% SDS, and 100 μg/ml sheared, denatured salmon sperm DNA. Duplicate filters were hybridized in the above buffer containing either 13 ng/ml probe 1198 or 16 ng/ml probe 1199 at an initial temperature of 68° C., and then at 42° C. overnight. The filters were washed twice for 15 min at room temperature in 6×SSC, 0.1% SDS, 0.05% sodium pyrophosphate, then for 5 min at 65° C. in the same buffer, and then dried and autoradiographed.

Of 40,000 clones screened, 8 hybridized to both probes, and were subjected to restriction analysis. Two overlapping clones which when combined span 1520 nucleotides were sequenced, with the results shown in FIG. 1. These two clones are designated pD10k-1 and pD10k-4, and are identified in FIG. 1. The arrow indicates the beginning of the mature 18 kd protein.

cDNA encoding the SP-5 protein: An oligomeric probe was synthesized which corresponded to the putative sequence of human 5 kd lung surfactant protein. A dog lung cDNA library was constructed as described above and screened. The cDNA isolated was approximately 800 bp. This was not a full-length cDNA, as Northern analysis showed that the full-length clone should be about 1.1 kb. The cDNA clone started approximately 30 amino acid residues upstream of the N-terminus of the mature dog 5 or 8 id protein. A possible clip site (Gln-Gln) which would give a protein of approximately 5 kd.

D.3. Human ASP DNAs

A human genomic library cloned into bacteriophage Charon 28 (Rimm, D.L., et al, *Gene* (1980) 12:301-310) was obtained from Dr. T. Maniatis, Harvard University. Approximately $1.5\times10^6$ phage were grown on *E. coli* K803, and plaque lysates were transferred to nitrocellulose filters as described by Benton, W. D., et al, *Science* (1977) 196:180-182. Isolation of the genomic clone gHS-15 which encodes the 32 kd human protein and expression of this gene have already been described.

In addition, cDNA libraries from human lung were prepared as described previously either by GC tailing or in λgt10. The recovery of cDNA encoding the 32 kd human ASP protein was also described in W086/03408.

Recovery of SP-18: As described in the published application, the cDNA library in λgt10 was screened on nitrocellulose filters using $1\times10^6$ cpm of the canine clone pD10k-1 described above (and identified in FIG. 1) in 40% formamide, 5×SSC, 0.05% SDS, 5×Denhardt's, 50 μg/ml yeast tRNA and 50 μg/ml salmon sperm DNA for 16 hr at 37° C. (The pD10k-4 segment or the full-length combination of the pD10k-1 and pD10k-4 clones can be used as well.) The filters were washed twice at 50° C. for 30 min in 2×SSC, 0.1% SDS, dried and autoradiographed. Of 40,000 plaques, two were positive, and one, destinated cDNA #3 containing a 1.5 kb insert was chosen for sequencing. The complete nucleotide and deduced amino acid sequence for the SP18 protein and its precursor are shown in FIG. 2. The mature SP18 protein begins, as shown in the Figure, at nucleotide 614 with the Phe at 201. It is believed that the carboxy terminus of the processed protein is the arginine at position 286. The 1.5 kb insert was excised and subcloned into EcoR1-cut pUC8; this plasmid, designated as ph18K-3, was deposited in *E coli* K-12 strain MC1061 with American Type Culture Collection under ATCC accession no. 67276.

The ph18K-3 cDNA insert was used to screen the human genomic library (supra) for the gene encoding the SP18 protein and its precursors. The sequences of the coding exons of the recovered gene are shown in FIG. 3. The mature amino terminus at Phe-201, is at nucleotide 3866; the numbering of the genomic nucleotide sequence begins with the first residue of the 7332 bp that were sequenced from the lambda clone.

The genomic and cDNA coding sequences differ at a single nucleotide, resulting in amino acid sequences for the precursor that differ by a single residue; Ile-131 of the cDNA appears as Thr-131 in the genomic clone. Thus, the genomic clone-encoded precursor contains two consensus sites for N-linked glycosylation (Asn-129:Thr-131 and Asn-311:Ser-313), the cDNA-encoded sequence contains only the latter glycosylation site. It is expected that cDNA clones encoding the genomic sequence are also present in the library.

Recovery of SP-5: For the SP5 proteins, a nucleotide mixture of 6 oligonucleotides was pooled (FIG. 4), which nucleotides were made to the N-terminal amino acid sequence of dog 8 kd and 5 kd protein. The human lung cDNA library in λgt10, prepared as described above, was screened, and 8 cDNAs encoding the SP5 protein were obtained. A cDNA clone starting approximately 19 residues upstream from the putative N-terminus of the mature SP-5 protein contains 820 bp and was inserted in lambda-phage, designated λh6k-3, and deposited with the American Type Culture Collection under ATCC accession no. 40294.

Two representative cDNA clones, Nos. 18 and 19, are shown in FIGS. 5 and 6. cDNA #18 contains the longest insert, of 862 bp, including 12 residues of poly(A); however, from Northern blot analysis, the mRNA encoding the SP-5 protein is 1–1.1 kb in length. cDNAs #s 18 and 19 differ by 4 nucleotides, underlined in the cDNA #19 sequence, which result in two amino acid differences: Asn-138 in #18 is Thr-138 in #19, and Asn-186 in #18 is Ser-186 in #19.

There are several N-terminal amino acid residues seen in the human 5 kd and 8 kd proteins, the primary two residues corresponding to Phe-24 and Gly-25 in FIGS. 5 and 6. The carboxy termini of the 5 kd and 8 kd proteins are now proposed herein as will be described in Section E.

(A canine lung library in pBR322 was prepared substantially as described above and screened with the human 820 bp clone. The isolated cDNA—designated pD6k-11— was about 800 bp , not a full-length cDNA. The clone started approximately 30 amino acid residues upstream of the N-terminus of the mature canine SP-5 protein, and contained a possible Gln-Gln clip site.)

D.4 Construction of Mammalian Expression Vectors

Vectors suitable for expression of the various ASP encoding sequences in mammalian cells, which are also capable of processing intron-containing, DNA were constructed. Expression is controlled by the metallothionein II (hMTII) control sequences, as described by Karin, M. et al, *Nature* (1982) 299:797–802.

An intermediate host vector, pMT was obtained by ligating the promoter into pUC8 as follows:

Plasmid 84 H (Karin, M., et al (supra)) which carries the hMTII gene was digested to completion with BamHI, treated with exonuclease Bal-31 to remove terminal nucleotides, and then digested with HindIII to liberate an 840 bp fragment containing nucleotides −765 to +70 of the hMTII gene (nucleotide +1 is the first nucleotide transcribed). The 840 bp fragment was isolated and ligated with HindIII/HincII digested pUC8 (Vieira, J., et al, *Gene* (1982) 19:259–268) and the ligation mixture transformed into *E. coli* MC1061. The correct construction of pMT was confirmed by dideoxy nucleotide sequencing.

In addition, a derivative of the pMT, pMT-Apo, containing C-terminal regulatory signals was also prepared. pMT-Apo harbors a portion of the human liver protein apoAI gene (Shoulders, C. C., et al, *Nucleic Acids Res* (1983) 11:2827–2837) which contains the 3'-terminal regulatory signals. A PstI/PstI 2.2 kb fragment of apoAI gene (blunt ended) was cloned into the SmaI site of the pMT polylinker region, and the majority of the apoAI gene removed by digestion with StuI, and religation. The resulting vector contains roughly 500 bp of the apoAI gene from the 3' terminus as confirmed by dideoxy-sequence analysis.

Additional expression vectors containing the SV40 viral enhancer were also constructed by insertion of an 1100 bp SV40 DNA fragment into the HindIII site preceding the MT-II promoter sequences in pMT. The SV40 DNA fragment spans the SV40 origin of replication and includes nucleotide 5171 through nucleotide 5243 (at the origin), the duplicated 72 bp repeat from nucleotide 107–250, and continues through nucleotide 1046 on the side of the origin containing the 5' end of late viral mRNAs. This HindIII 1100 bp fragment is obtained from a HindIII digest of SV40 DNA (Buchman, A. R., et al, *DNA Tumor Viruses,* 2nd ed. (J. Tooze, ed.), Cold Spring Harbor Laboratory, New York (1981), pp. 799–841), and cloned into pBR322 for amplification. The cloning vector was cut with HindIII, and the 1100 bp SV40 DNA fragment isolated by gel electrophoresis and ligated into HindIII-digested, CIP-treated pMT. The resulting vectors, designated pMT-SV(9) and pMT-SV(10), contain the fragment in opposite orientations preceding the MT-II promoter. In pMT-SV(9), the enhancer is about 1600 bp from the 5' mRNA start site; in the opposite orientation SV(10) it is approximately 980 bp from the 5' mRNA start site. Both orientations are operable, but the orientation wherein the enhancer sequences are proximal to the start site provides higher levels of expression.

The 500 bp apoAI fragment was inserted into pMT-SV(10) by isolating this fragment, obtained by digestion of pMT-Apo (described above) and ligating the isolate into EcoRI/BamHI digested pMT-SV(10) to obtain the desired host vector: pMTApo10.

This host vector was digested with BamHI, blunted and ligated to the cDNA sequences obtained from the clone #3 of 1275 bp encoding SP-18 precursor, shown in FIG. 2 as a blunted fragment. This was done by isolating an EcoRI/BamHI (partial) fragment from cDNA #3 (FIG. 2) avoiding the BamHI (partial) fragment from cDNA #3 (FIG. 2) avoiding the BamHI site at nucleotide 663 and subcloning into EcoRI/BamHI pUC9 the desired fragment was excised with EcoRI and HindIII, blunted with Klenow, and then inserted into pMTApo10. The resulting vector, pMT(E):SP- 18–40k, was transformed into CHO cells as described below.

In a similar manner, the blunted EcoRI insert of the SP-5 clones of FIGS. 5 and 6 was placed into BamHI digested pMTApo10 to obtain pMT(E):SP-5 vectors, and transformed into CHO cells.

D.5. Expression in Mammalian Cells

Chinese hamster ovary (CHO)-K1 cells were grown on medium composed of a 1:1 mixture of Coon's F12 medium and DME21 medium with 10% fetal calf serum. The competent cells were co-transformed with the vector of interest and pSV2:NEO (Southern, P., et al, *J Mol Appl Genet* (1982) 1:327–341). pSV2:NEO contains a functional gene conferring resistance to the neomycin analog G418. In a typical transformation, 0.5 μg of pSV2:NEO and 5 μg or more of the expression vector DNA were applied to a 100 mm dish of cells. The calcium phosphate-DNA co-precipitation according to the protocol of Wigler, M., et al, *Cell* (1979) 16:777–785, was used with the inclusion of a two minute "shock" with 15% glycerol in PBS after four hours of exposure to the DNA.

Briefly, the cells are seeded at 1/10 confluence, grown overnight, washed 2× with PBS, and placed in 0.5 ml Hepes-buffered saline containing the $CaPO_4$.DNA co-precipitate for 15 min and then fed with 10 ml medium. The medium is removed by aspiration and replaced with 15% glycerol in PBS for 1.5–3 min. The shocked cells are washed and fed with culture medium. Until induction of MT-II-controlled expression, the medium contains F12/DMEM21 1:1 with 10% FBS. A day later, the cells are subjected to 1 mg/ml G418 to provide a pool of G418-resistant colonies. Successful transformants, also having a stable inheritance of the desired plasmid, are then plated at low density for purification of clonal isolates.

The transformants are assayed for production of the desired protein, first as pools, and then as isolated clones in multi-well plates. The plate assay levels are somewhat dependent on the well size—e.g. results from 24 well plates are not directly comparable with those from 96 well plates. Clones which are found by plate assay to be producing the protein at a satisfactory level can then be grown in production runs in roller bottles. Typically, the levels of production are higher when the scale-up is done. For this reason, typically 100–200 or more individual clones are assayed by various screening methods on plates and 5–10 of the highest producers are assayed under production conditions (roller bottle).

Pools of transformed cells were grown in multi-well plates and then exposed to $5\times10^{-5}$ to $1\times10^{-4}$ zinc ion concentration to induce production of ASP.

Semiconfluent monolayers of individual cell lines growing in McCoy's 5A medium with 10% FBS were washed with phosphate-buffered saline (PBS) and refed with McCoy's containing 10% FBS, $1\times10^{-4}$ zinc chloride, and 0.25 mM sodium ascorbate. (Ascorbate may be helpful in mediating the hydroxylation of proline residues.) Twenty-four hours post induction, the cells were washed with PBS and refed with serum-free McCoy's containing the zinc chloride and ascorbate. After 12 hours, the conditioned media were harvested.

A pool of transformed cells was induced with $ZnCl_2$ as described above, and labeled with $^{35}S$-methionine. After a 12 hr labeling period, culture medium was harvested as described and immunoprecipitated with antisera raised against the human SP-18 ASP. Samples were then subjected to SDS-PAGE in a 15% gel, with the results shown in FIGS. 7*a* and 7*b*.

Figure 7B:
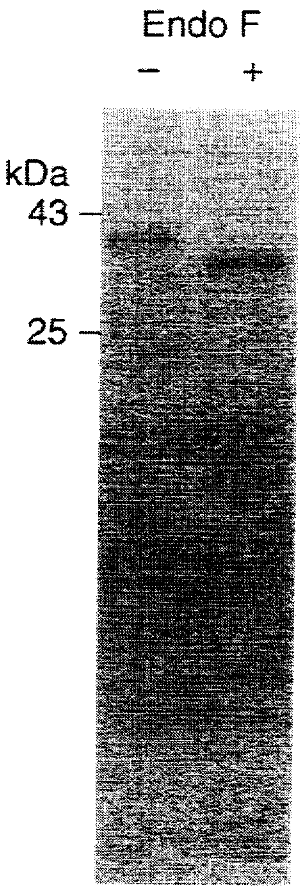

In FIG. 7*a*, lane M represents molecular weight standards, lane A represents immunoprecipitated proteins from untransformed CHO cells, and lane B represents immunoprecipitated protein from the pMT(E):SP18-40K transformed pool. In FIG. 7*b*, the immunoprecipitated protein from the transformed pool was digested with endoglycosidase f for one hour, then electrophoresed as in FIG. 7*a*. Lane A is untreated control, lane B is the digested sample.

As shown in FIG. 7*a*, 43 kd and 25 kd precursor proteins are produced by the transformed cells; the smaller molecular weight proteins shown in FIG. 7*a* are not reproducible. The results of FIG. 7*b* show the 43 kd precursor is glycosylated. The size of the unglycosylated, immunoprecipitated protein is that predicted for the full-size precursor.

Cold protein produced by the above induced pool was subjected to Western blot using antisera raised against a peptide spanning residues 336–353 of the precursor. It is believed the 25 kd product represents a 181 amino acid sequence spanning Phe-201:Leu-381, containing a N-linked glycosylation site.

D.6. Additional Vectors

Analogous vectors were constructed using standard site-specific mutagenesis techniques to provide sites for in vitro cleavage of the precursor protein which was, apparently, produced in CHO cells from the full length sequence. In one such construct, the 381 amino acid precursor was modified to replace each of the Gln-199:Gln-200 and Arg-286:Ser-187 by Asn:Gly, to provide sites cleavable by hydroxylamine (which cleaves between Asn and Gly). Cleavage of the precursor thus produced with hydroxylamine generates the putative mature form, with an additional gly residue at the amino terminus, and with the putative carboxy-terminal Arg-286 changed to an Asn residue.

In another construct, Phe-201 and Ser-87 are changed to Asp residues. Cleavage with acid (between Asp and Pro) yields a mature form of the SP-18 protein missing the N-terminal Phe-201, and with an additional carboxy-terminal Asp residue.

An additional construct allows in vitro processing of the precursor with a more gentle enzymatic procedure, employing Staph V8 peptidase, which cleaves after Glu residues. Advantage is taken of natural Glu residues at Glu-198 and Glu-291 by converting the Glu-251 to Asp. The 43 kd precursor is cleaved with staph V8 to yield the putative mature SP-18 protein with an additional Gln-Gln at the amino terminus, and Pro-Thr-Gly-Glu at the carboxy terminus. In an additional construct, Glu residues can be placed in positions 200 and/or 287.

D.7. Expression in Bacteria

The unglycosylated form of the SP-18 protein can be produced in bacteria as a 181 amino acid precursor representing met-preceded residues 201–381 or as a hydroxylamine-cleavable fusion protein precursor with a 15 residue β-galactosidase leader. A modified cDNA encoding amino acids 201–381 of the cDNA, preceded by ATG is inserted into the Trp controlled vector, pTrp-233 (pTrp host vector), between the EcoRI site and the HindIII site to give pTrp-0. This construct produces a protein of M.W. 20 kd. An analogous construct in pBGal host vector, pBGal-20 contains the same sequences of SP-18 cDNA #3 fused to a 15 residue β-galactosidase leader through a hydroxylamine-sensitive Asn-Gly doublet, and produces a fusion protein of MW=22 kd. Details of the construction are given in D.11 below.

The pTrp-20k and pBGal-20k plasmids were used to transform *E. coli* W3110 to ampicillin resistance. Rapidly growing cultures of pTrp-20/W3110 or pBGal-20/W3110 in M9 medium (1×M9 salts, 0.4% glucose, 2 mg/ml thiamine, 200 μg/ml $MgSO_4.7H_2O$, 0.5% casamino acids, 100 μg/ml IAA (3-β indoleacrylate, Sigma I-1625) to induce the trp promoter.

The induced cells were allowed to grow for 2 hours before labeling with $^{35}S$ methionine (100 μCi/ml cells) for 10 minutes. The labeling was stopped by the addition of 350 μl cold 20% TCA per ml of cells; the TCA pellets were washed with acetone, and then resuspended by boiling in SDS-PAGE sample buffer, and subjected to PAGE in a 15% gel.

Figure 8:
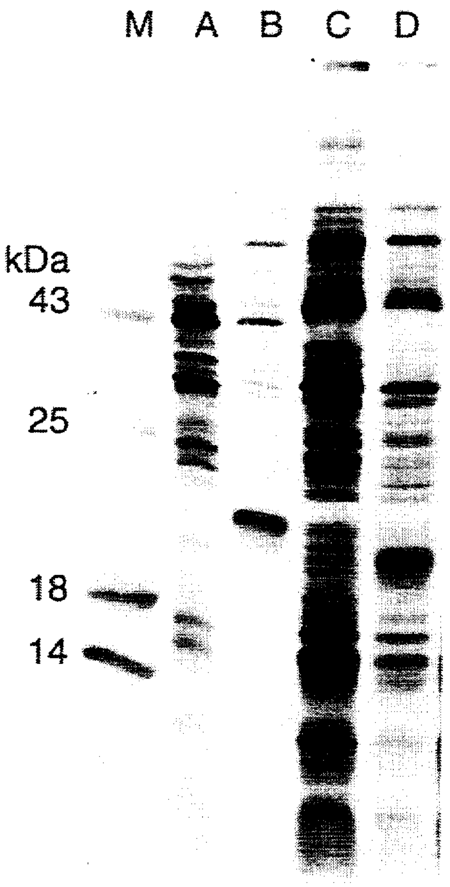
FIG. 8 shows an SDS gel obtained from bacterial transfected with expression vectors for human 18 kd protein (and controls) labeled with $^{35}S$ methionine.

FIG. 8 shows the results of this procedure: lane M is size standards; lane A is pβgal host vector/W3110; lane B is Bgal-20/W3110; and lane D is pTrp-0/W3110. Lanes B and D show major labeled proteins of 22 kd and 20 kd, respectively, which are not present in lanes A and C.

Figure 9:
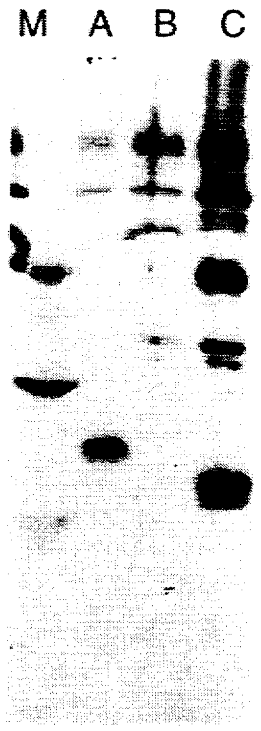
FIG. 9 shows a Western blot of bacterial extracts corresponding to those of FIG. 8.

Cold extracts of the induced cells were prepared the same way, subjected to PAGE, then Western blotted to nitrocellulose, using antisera raised against a peptide corresponding to amino acids 336–353, and then with $^{125}I$-Protein a. In FIG. 9, lane A is Bgal-20/W3110, lane B is pTrp host vector/W3110, and lane C is pTrp-20/W3110. It is clear that both pTrp-0 and Bgal-20 show immunospecific proteins of the predicted molecular weight.

Vectors encoding modified SP-18 protein sequences providing cleavage sites as set forth above for expression in bacteria were also prepared as follows. In pTrp-20, codons encoding Arg-286:Ser-287 were altered to encode Asn-Gly; introducing the hydroxylamine-sensitive cleavage site, or the codon for Ser-287 was replaced by a codon for Asp, resulting in the acid-sensitive Asp-Pro cleavage site, or the codon for Glu-251 was replaced with a codon for Asp, allowing cleavage with Staph V8 at Glu-291 without cleaving the desired protein. Also, in both pTrp-20 and pBGal-20, the sequences 3' to the putative carboxy terminal Arg-286 were deleted and replaced by a stop codon. Neither construct resulted in labeled protein of proper size after induction.

Analogous to pTrp-20, the desired fragment of the cDNA #18 (FIG. 5) extending from gly-25 preceded by ATG to the carboxy-terminal Ile-197 of the Sp-5 "precursor" was inserted into EcoRI/HindIII digested pTrp-233 to give pTrp-5 and into pBGal host vector to give pBGal-5 wherein the SP-5 sequence is fused to a β-galactosidase leader through a hydroxylamine-sensitive Asn-Gly.

Also, cleavage with Staph V8 of the protein expected from this construct at the Glu preceding Phe-24 and at Glu-66 yields mature 5 kd protein if the putative C-terminus is correct.

These constructs are transformed into *E. coli* W3110 and expressed as described above.

D.8. Purification of the 32K Proteins

The 32K proteins have a striking amino acid homology with circulating mannose-binding proteins, and also contain residues common to the carbohydrate-binding domains of other lectins. It is believed that carbohydrate recognition may be an important property of the 36 kd ASP protein as well as the other 32K proteins in the regulation of surfactant metabolism or in other functions such as alveolar immunity. It is possible to exploit the mannose affinity of the proteins so as to purify them using carbohydrate affinity chromatography. The chromatographic purification may be carried out either on an immobilized glycoprotein containing a high proportion of mannose residues (e.g., yeast mannan or invertase) or on columns constructed directly with mannose coupled to agarose.

The 36 kd protein isolated from lung lavage was found to bind to immobilized monosaccharides with a broad specificity in the presence of 1 mM $Ca^{2+}$. A purification procedure according to this preferred embodiment was carried out as follows. Cell culture media (typically 8–16 liters) containing 2.5 mM $CaCl_2$ was loaded directly onto a 60 ml mannose-agarose column (Selectin-10, Pierce Chemical) at a rate of about 240 ml/hr. The column is washed, preferably with 10 column volumes of a solution containing 5 mM Tris, 1 mM $CaCl_2$ and 25 mM NaCl, pH 7.5. The bound protein was quantitatively recovered by elution with 2 mM EDTA or the hapten sugar in the presence of calcium ions. A preferred procedure is elution with 2–3 column volumes of a basic solution of about pH 10, a preferred solution containing about 100 mM sodium borate (pH 10.0). After four runs, the column may be stripped with 4M urea and reequilibrated in the PBS or stored in 2% benzyl alcohol.

The data set forth in the following table gives the percentage of recovered protein bound in the presence of calcium ions. The values represent the mean of from two to seven experiments. The threshold $Ca^{2+}$ concentration for binding was 0.6 mM and maximal binding occurred with 1 mM $Ca^{2+}$. $Ba^{2+}$, $Sr^{2+}$ and $Mn^{2+}$ could substitute for $Ca^{2+}$. The 36 kd protein was found to bind to carbohydrate at a pH of 5.0, although binding activity was lost upon heat treatment or reduction of disulfide bonds.

| | Fuc | Man | Glc | Gal | GalNAc | GlcNAc |
|---|---|---|---|---|---|---|
| Dog* | 94 | 85 | 64 | 49 | 22 | 8 |
| Human* | 100 | 100 | 100 | 100 | 7 | 2 |

*Data is expressed as the percentage of recovered protein (94 ± 8% of applied) bound in the presence of $Ca^{2+}$. The values are the mean of 2–7 experiments. The threshold $Ca^{2+}$ concentration for binding was 0.6 mM and maximal binding occurred with 1 mm $Ca^{2+}$.

Alternative columns suitable for purification of the 32K proteins include: (1) mannose-Sepharose, prepared by coupling of mannose to Sepharose 6B (Pharmacia) with divinyl sulfone (see, e.g., Fornstedt, N. and Porath, J. (1975) *FEBS Lett.* 57, 187–191); (2) invertase-Sepharose, prepared by coupling of invertase to Sepharose 6B using the CNBr method (see, e.g., Porath, J. (1974) *Methods Enzymol.* 34, 13–30); (3) galactose-Sepharose; and (4) combinations of the foregoing. These columns may, as noted, include various combinations of carbohydrates and resin and may be used sequentially to ensure substantially complete removal of impurities.

D.9. Activity of the ASP Components

The ability of the isolated ASP components to enhance the formation of lipid film at an air/aqueous interface was assessed in vitro using the method described by Hawgood, S., et al, *Biochemistry* (1985) 24:184–190.

Briefly, a preparation of phospholipid vesicles with the appropriate ratio of test proteins is added carefully in a small volume to the bottom of a teflon dish containing aqueous buffer, a magnetic stirrer, and a platinum plate suspended at the surface of the buffer and attached to a strain gauge. Changes in surface tension registered on the strain gauge are recorded as a function of time upon starting the stirrer.

10K proteins were added to the phospholipid by mixing a chloroform solution containing them with a 2:1 v/v chloroform:methanol solution of the lipid. The solvents were evaporated, and the solids hydrated in buffer to obtain vesicles. 32K proteins can be added in aqueous solution directly to a suspension of the vesicles, and association with and aggregation of the vesicles can be detected by turbidity measurements.

As reported by Hawgood, et al (supra), 32K canine ASP was capable of aggregating phospholipid vesicles and of enhancing the formation of film when included in the phospholipid vesicles, when the phospholipids were those obtained from the canine lung surfactant complex. The activity of the proteins of the invention is assessed using the same procedures for measuring aggregation and film formation enhancement as set forth in Hawgood.

Both the phospholipid preparation from canine lung prepared as described above (300 μg) and a synthetic mixture of phospholipids were used. The synthetic phospholipid contained 240 μg of commercially available DPPC and 60 μg egg PG, and is much more reluctant to form films than is the natural lipid. However, the test phospholipid was chosen so as to dramatize most effectively the activity of the proteins.

Figure 10:
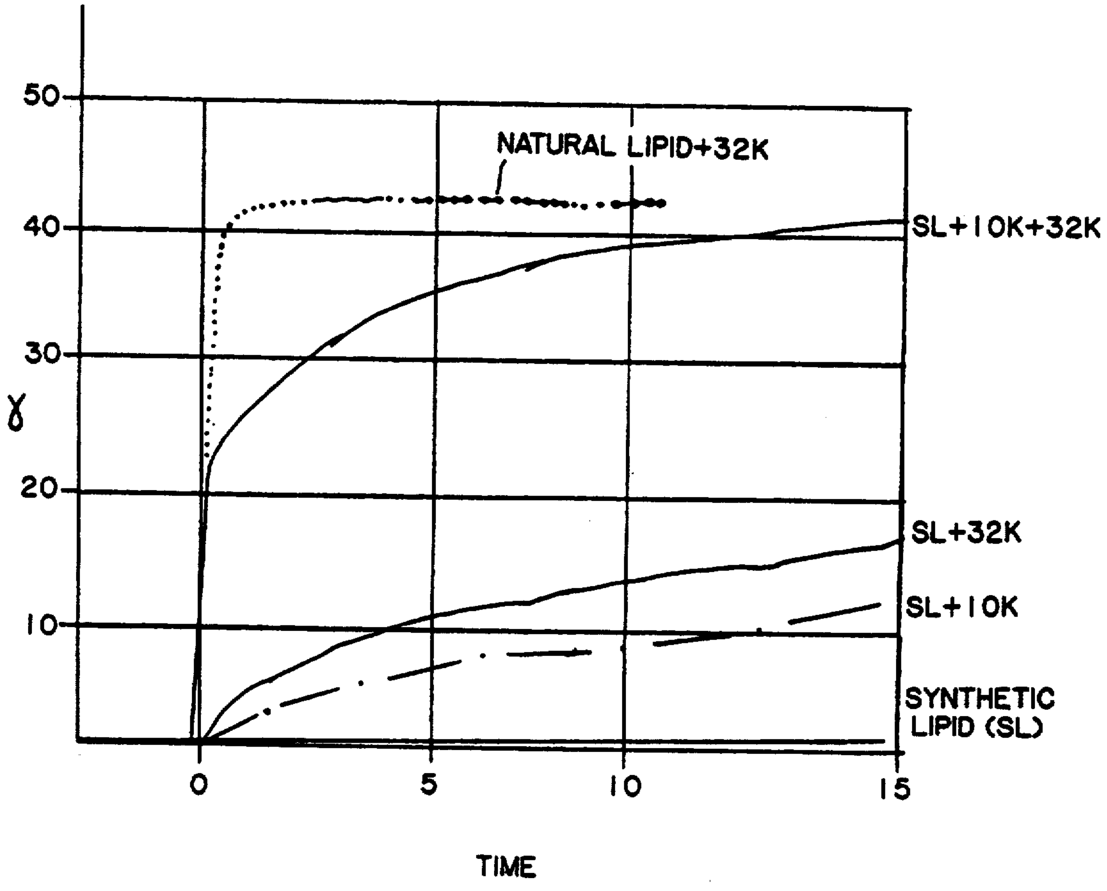
FIG. 10 shows the result of an in vitro determination of the ability of various ASP proteins to enhance surface tension-lowering by phospholipids.

The 32K protein and the mixture of 10K ASP were isolated from canine lung as described above. While the addition of 60 μg of the 32K protein was able to enhance film formation by the "natural" phospholipid obtained from lung almost to the level exhibited by the complex per se, it only moderately enhanced film formation using synthetic lipid. Similar results were obtained for addition of 13 μg of the 10K protein alone. However, when 13 μg of the 10K preparation was incubated with the synthetic phospholipid vesicles prior to the addition of 60 μg of 32K protein, film formation occurred at a rate and to a degree comparable to that of the natural complex per se. These results are shown in FIG. 10.

Figure 11:
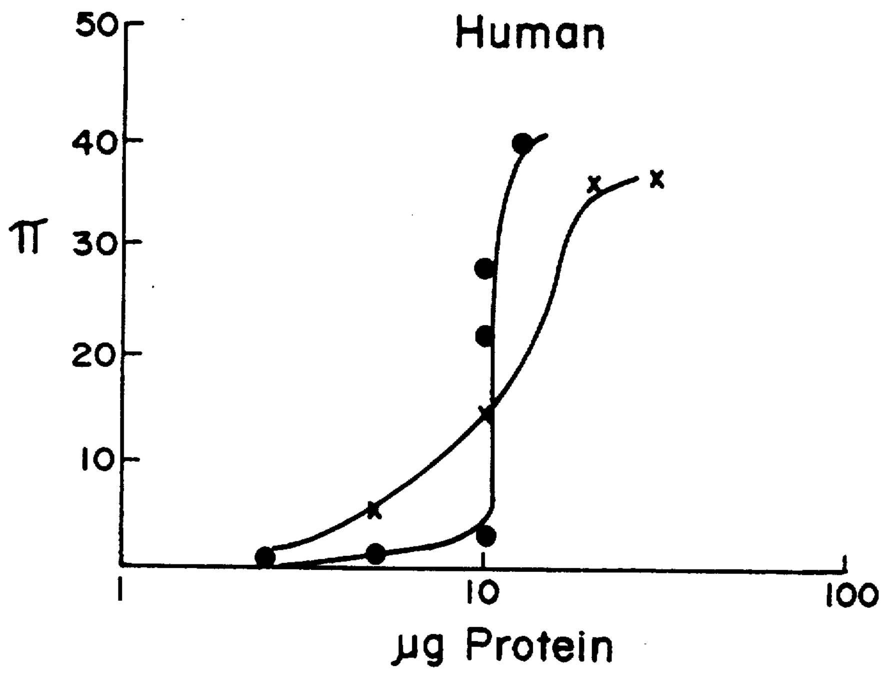
FIG. 11 shows the results of an additional in vitro determination of the ability of human 18 kd and 5 kd proteins to enhance surface tension lowering by phospholipids.
Figure 12:
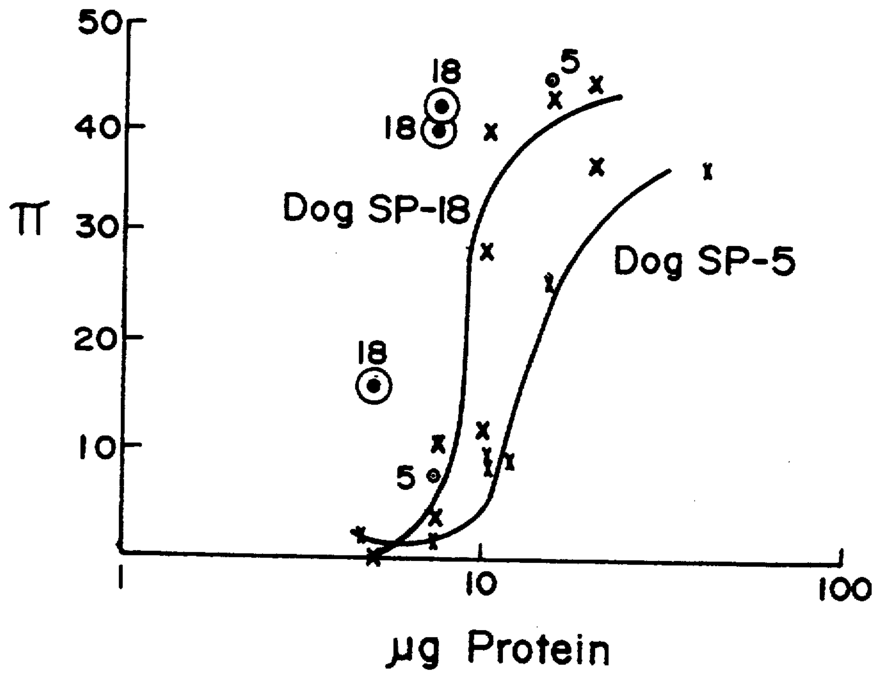
FIG. 12 shows the results corresponding to those of FIG. 11 for the canine proteins, with and without the addition of 32 kd protein.

The results for individual human and canine 5 kd and 18 kd proteins are shown in FIGS. 11 and 12, plotting surface pressure after 3 minutes (x axis) versus protein concentration (y axis). As shown in FIG. 11, the maximum pressure attained is 40–45 mN/m, and either 5 kd or 18 kd cause the spreading of lipids at about 10 μg. This corresponds to a phospholipid-to-protein ratio of 10:1 since 100 μg of lipid was used in all cases; the lipid mixture was DPPC:PG (7:3), but 8:2 and 9:1 ratios gave no significant difference in results.

For the canine proteins shown in FIG. 12, the results are identical to those for the human protein. FIG. 12 also shows the results of experiments in which recombinantly produced r32K was added to the 18 kd or 5 kd protein. The synergy between the proteins is shown in the circled dots. Ten μg 32 kd protein was added to 5 μg and 7.5 μg for 18 kd, and 7.5 and 11 μg for 5 kd protein.

Bovine 18 kd and 5 kd proteins gave identical results to the canine and human proteins.

D.10. In Vivo Tests

The control surface active material (SAM) for in vivo testing was prepared as follows. Lungs of young adult rabbits are lavaged with saline. Healthy rabbits are anesthetized through the ear vein with 3 cc of sodium pentobarbital. The trachea is exposed and a 3-way stopcock with a tube attached is inserted into the trachea and secured. The chest is opened, the chest walls are removed, and the pulmonary artery is catheterized with a size 8 feeding tube from the heart. The circulation is flushed with 50 ml of normal saline while ventilating the lungs through the tracheal tube with a 60 ml syringe, and the lungs are then carefully removed with the trachea intact. Sixty ml of normal saline are instilled into the lungs through the tracheal tube, the lungs are then gently massaged for one minute, and the saline is withdrawn. Lavage is repeated four times, and the washings are pooled. Cell debris is removed from the lavage fluid at room temperature by centrifugation at 1000×g for two hours. The pellet is suspended in 0.1N saline plus 2M $CaCl_2$ at a final concentration of 10 mg/ml phospholipid. Concentration is adjusted by extracting the lipids with chloroform and methanol and measuring lipid phosphorus. In the bubble tensitometer this material gives rapid adsorption (time constant 0.3 sec or less) and minimum surface tensions of 0 to 3 mN/m on 50% reduction of area. Maximum tension on expansion was 32 to 35 mN/m.

The subject and apparatus used for in vivo testing are as follows. Healthy, young, time-dated pregnant does are obtained from White Hare Rabbitory of Missouri. At 21 or 22 days gestation the does are air-shipped and are checked upon arrival to assure that they are pregnant and healthy. Does are housed in standard large rabbit cages in the rabbit facility (1492-S) and are reexamined the day before use.

Four plethysmographs are constructed with 80-inch lengths of 2-inch diameter acrylic cylinder to which are affixed a 3-inch long chimney of ½-inch acrylic tubing (id, 0.5 inch). The chimney is filled with enough cotton gauze to create a low resistance to air flow in and and out of the plethysmograph. Flow in and out of the chamber is determined by measuring the differential pressure change between the inside of the plethysmograph and the room. (Time constant 0.1 seconds.) Leads are taken from the end of the main cylinder to a pressure transducer (Validyne DP45, Validyne Engineering Company, Horthridge, CA) and to a calibrating syringe. When conducting experiments, the electrically integrated flow (volume) signal is frequently calibrated with the syringe. The other end of the main cylinder is sealed with a 2–8nch rubber stopper through which were placed two 4-inch metal rods and through which were pulled three ECG leads. Cotton sheeting is placed between the two metal rods forming a sling on which the experimental animal is placed. Bayonet-type electrodes are attached to the ECG leads. An adapter is placed through the stopper so that the hub of the tracheal angiocath can be connected to a flow-through manifold which in turn is attached to the tubing from a respirator (Mark VIII, Bird Respirator Company, Palm Springs, Calif.). The external deadspace of the airway is 0.05 to 0.07 ml. Airway pressure is measured in the manifold with an Alltech MSDICE/1 transducer (Alltech, City of Industry, Calif.). The plethysmograph calibration is linear at volumes of 0.01 to 1 ml and at frequencies of 10 to 100 oscillations per minute. The four plethysmographs are mounted in a single water bath heated to 37° C. Each animal has its own ventilator. Switching devices permit flow, volume, airway pressures and ECG to be recorded from each rabbit sequentially on a Brush recorder. Usually three animals are used for one minute in every five minutes from each is recorded.

The procedure used is as follows. Rabbit pups of 27 d±4 hr gestation were used. After giving the dose spinal anesthesia (1 ml pontocaine), the abdomen is opened and the uterus exposed. Two minutes before opening the uterus, each fetus receives 15 mg/kg pentobarbital and 0.1 mg/kg pancuronium intraperitoneally. When fetal movement stops, the fetuses are anesthetized and quickly delivered. After weighing, three pups of about the same weight are chosen for the experiment. Pups with obvious anomalies are not studied. Pups most be between 22 and 40 grams weight (mean±2 SD). Tracheas are cannulated with 180 gauge angiocaths while they are kept warm under radiant heat after cannulation, 0.2 ml of either saline, SAM or test substance (warmed to 37° C. in $H_2O$ bath and then passed through a 25 g needle×5 to insure uniform mixing of the material) are put into the trachea of the three matched pups from each litter while gently squeezing the chest until lung fluid appears at the needle hub in order to create a fluid-to-fluid interface. The treatment is followed by 0.45 ml of air.

All test substances (but not saline or SAM controls) contain 50 mg phospholipid/kd delivered as 0.2 ml per animal at 10 mg phospholipid/ml. Concentration and dose are constants for each study. The animals are placed on the slings, and the ECG electrodes attached and the tracheotomy tube connected to an adapter connected to a respirator. The average elapsed time from delivery to the beginning of assisted ventilation is 10 minutes; maximum elapsed time is 15 minutes. ventilation is begun with oxygen at a frequency of 48 breaths/-minute using an inspiratory time of 0.35 seconds. For the first minute, the ventilatory settings are the same for all animals; inspiratory time 0.35 seconds, peak inspiratory pressure 40 $cmH_2O$. After the first minute the inspiratory pressure is adjusted to keep the tidal volume at 6.5-7.5 ml/kg. Animal weight is about 30 g so this is achieved with an absolute volume of about 0.21 ml. The flow, tidal volume and airway pressure are recorded every five minutes for each of the three littermates. Animals are ventilated for 30 minutes.

Data from all animals in a set are rejected if one member develops an air leak or dies of other causes.

After 30 minutes ventilation the tracheal tubes are closed with stopcocks and the lungs are allowed to degas for 10 minutes. Then each air-filled angiocath is connected to a horizontal, calibrated length of 5 mm plastic tubing containing 3 ml of air at the lung end and dyed water at the other end. The fluid-filled ends of three plastic tubes are connected via a manifold to a single reservoir of dyed water, whose surface is at the same level as the tubes. This reservoir can be raised in 50 cm water steps which correspondingly increase the pressure in the tubing and lungs. As the pressure increases or decreases, gas enters or leaves the lungs, displacing the fluid column, allowing measurement of the changes in gas volumes. This apparatus is similar to that described by Robertson, B., *Lung* (1980) 158:57-68. The pressure is raised stepwise from 0 to 5, 10, 15, 20, 25, 30 $cmH_2O$, with a pause for one minute at each level before recording the volume change. After one minute at 20 mm $H_2O$, the pressure is decreased by 5 cm $H_2O$ decrements, again maintaining each pressure for one minute before recording the volume. Each volume measurement is corrected for compression. During the studies the animals are kept at 37° C. by placing them in a water bath just below the surface.

Data are obtained for $P_{INS}$, compliance (C) and volume at specific pressures (Vp). $P_{INS}$ is the pressure required to maintain a net lung volume; lower numbers, of course, indicate efficacy. Compliance, a measure of how easily the lungs are inflated, is also measured, and higher volumes are desired. Vp is the volume in $cm^3$ of the lungs at the noted pressure in cm of water. The results are as follows.

For $P_{INS}$ at 30 minutes, the results are as in Table 1 (PL is phospholipid; 32K protein is human 32 kd ASP produced in CHO cells; 10K is a mixture of 5 kd, 8 kd and 18 kd isolated native human proteins).

TABLE 1

| Treatment | n | $P_{INS}$ |
|---|---|---|
| SAM | 13 | 18 ± 4 |
| Saline (control) | 9 | 31 ± 1 |
| PL alone | 4 | 32 ± 1 |
| PL + 32K | 3 | 28 ± 5 |
| PL + 10K | 8 | 17 ± 2 |
| PL + 10K (200:1) + 32K (4:1) | 8 | 20 ± 5 |
| PL + 10K (200:1) | 5 | 25 ± 8 |
| PL + 18 kd (50:1) | | 21, 22, 20 |
| PL + 5 kd (50:1) | | 19 |

As shown in Table 1, 32K alone is minimally effective, while the 10K mix or 5 kd or 18 kd proteins alone are reasonably effective. Addition of the 32K protein to the 10K mix, however, enhances the effectiveness synergistically.

For compliance, table 2 shows similar results.

TABLE 2

| Treatment | n | Compliance |
|---|---|---|
| SAM | 13 | 0.441 ± 0.113 |
| Saline (control) | 9 | 0.243 ± 0.025 |
| PL alone | 4 | 0.219 ± 0.028 |
| PL + 32K | 3 | 0.247 ± 0.029 |
| PL + 10K | 8 | 0.467 ± 0,078 |
| PL + 10K (200:1) + 32K (4:1) | 8 | 0.401 ± 0.041 |
| PL + 10K (200:1) + | 5 | 0.328 ± 0.176 |
| PL + SP-18 (50:1) | | 0.4 ± 0.045 |
| PL + 5 kd (50:1) | | 0.4 ± 0.045 |

Again the 10K mix or the 18 kd and 5 kd proteins show good activity, and while the 32K is much less effective, addition of the 32K protein greatly enhances activity of the 10K mix.

Tables 3 and 4 show $V_{30}$ and $V_5$ (30 cm water and 5 cm water), respectively.

TABLE 3

| Treatment | n | $V_{30}$ |
|---|---|---|
| SAM | 12 | 72 ± 9 |
| Saline (control) | 4 | 23 ± 11 |
| PL alone | 1 | 26 |
| PL + 32K | 3 | 38 ± 15 |
| PL + 10K | 7 | 65 ± 9 |
| PL + 10K (200:1) + 32K (4:1) | 7 | 58 ± 11 |
| PL + 10K (200:1) + | 2 | 55 ± 33 |

TABLE 4

| Treatment | n | $V_5$ |
|---|---|---|
| SAM | 12 | 56 ± 9 |
| Saline (control) | 4 | 11 ± 7 |
| PL alone | 2 | 14 |
| PL + 32K | 3 | 20 ± 7 |
| PL + 10K | 7 | 48 ± 9 |
| PL + 10K (200:1) + 32K (4:1) | 7 | 45 ± 10 |
| PL + 10K (200:1) + | 2 | 43 ± 27 |

The results track those obtained for $P_{INS}$ and compliance in the preceding tables.

Results obtained with the corresponding bovine proteins are similar.

D.11. Host Vectors pTrp233 is prepared from pKK233-2, which is described in detail in Amann, E., et al, *Gene* (1985) 40:183–190, by replacing the tac promoter of pKK233-2 with a synthetic trp promoter of the nucleotide sequence shown in FIG. 14. The NdeI site of the starting plasmid is eliminated by digesting pKK233-2 with NdeI, blunting with Klenow and religating. The NdeI-minus product was then digested with EcoRI and PstI, and ligated to an EcoRI/PstI digest of the synthetic trp promoter of FIG. 14 to obtain the desired vector, pTrp233. To prepare pBGal host vector, pTrp233 was digested with EcoRI, purified on a gel, and blunted with Klenow. The plasmid was religated and amplified in *E. coli* to give the corresponding plasmid lacking the EcoRI site. A synthetic oligonucleotide sequence encoding the amino terminus of β-galactosidase followed by 6 threonine residues

```
        beta-gel                (thr)6
[1] TATGACCATGATTACGAATTTAACCACCACCACCACCACCACCGAATTCATTA      [3]
[2]   ACTGGTACTAATGCTTAAATTGGTGGTGGTGGTGGTGGCTTAAGTAATTCGA     [4]
    NdeI                                        EcoRI    HindIII
```

was ligated into NdeI/HindIII digested intermediate plasmid, and plasmid containing the insert (pBGal host vector) identified by susceptibility to EcoRI cleavage.

To construct pTrp-20, a portion of the SP-18 cDNA #3, along with a synthetic fragment, was ligated into NdeI/HindII digested pTrp-233. The SP-18 fragment ligated into pUC-9 described above was excised by digesting with PstI (cuts at nucleotide 694) and with HindIII (cuts past the 3′ end in the plasmid polylinker). Two oligonucleotides were prepared, which, when annealed, encode the residues upstream of nucleotide 694 to the N-terminus (residue 201) and a preceding methionine (ATG): TATGTTCC-CCATTCCTCTCCCCTATT GCTGGCTCTGCA and GAGCCAGCAATAGGGAGAGGAATGG-GGAACA. These oligonucleotides were annealed, ligated to the excised cDNA, and inserted into the digested vector to obtain pTrp-20.

To construct pBGal-20, an analogous procedure using EcoRI/HindIII digested pBGal host vector, PstI/HindIII excised SP-18 DNA, and the filler nucleotides: AATTGAACGGTTTCC-CCATTCCTCTCCCCTATTGCTGGCTC TGCA and GAGCCAGCAATAGGGGAGAGGAATGG-GGAAACCGTTG, to give pBGal-20.

Vectors for the expression of the gene encoding shorter forms of SP-18 were constructed from pTrp-20 or pBGal-20. To construct pTrp-9, pTrp-20 was cut with NcoI (nucleotide 846) and HindIII, and rejoined with the annealed oligonucleotides CATGGAT-GACAGCGCTGGCCCAGGGTA and AGCT-TACCTTGGGCCAGCGCTGTCATC. pBGal-9 was constructed in a completely analogous manner using pBGal-20 as starting material.

To construct vectors encoding SP-5, cDNA #18 (FIG. 5) was digested with SmaI (nucleotide 94–nucleotide 680) and the SmaI-excised fragment inserted into the SmaI site of pUC8. From the cloned gene, the fragment excised by digestion with ApaLI (nucleotide 123) and HindIII (linker) was ligated with NdeI/HindIII digested pTrp-233 and the joining annealed nucleotides TATGGGCATTCCCTGCTGCCCAG and TGCACTGGGCAGCAGGGAATGCCCA, to obtain pTrp-5.

Similarly, pBGal-5 (N:G) and pGGal-5 (V8) were constructed using the same cDNA excised fragment, pBGal host vector cut with EcoRI and HindIII, and the nucleotide pairs: AATTCAACG-GCATTCCCTGCTGCCCAG and AATTCG-GCATTCCCTGCTGCCCAG and TGCACTGG-GCAGCAGGGAATGCCG, respectively.

E. Identification of Termini, 5 kd and 18 kd Proteins

E.1. The 5 kd Protein

The carboxy terminus of the 5 kd protein in the 10K mixture proved difficult to ascertain, as the protein is derived from a large precursor having a molecular weight of about 20,500 D. The carboxy terminus of the canine 5 kd protein was ultimately determined by the inventors herein, using mass spectrometry, to be His-59 (see FIG. 15). By analogy, it may be assumed that the human 5 kd protein has the identical C-terminus because the amino acid homology in this region is extremely high. Thus, the carboxy terminus of the human 5 kd protein should be His-54 (see FIG. 15).

The N-terminus of the 5 kd protein was determined by direct amino acid sequencing to be phenylalanine, but truncated species were also found having glycine and isoleucine as alternative N-termini (see FIGS. 14 and 15).

E.2. The 18 kd Protein

The carboxy terminus of the 18 kd protein in the 10K mixture was analyzed using quantitative amino acid composition, amino acid sequencing of the protein beginning at the N-terminus, carboxypeptidase Y digestion (an enzyme which cleaves amino acids from the C-terminus of proteins), and mass spectrometry.

Sequence analysis of the canine and bovine 18 kd proteins, after cleavage at methionine with cyanogen bromide, indicated the C-terminus of the canine protein to be His-279 and that of the bovine protein to be Ser-278. Enzymatic analysis using carboxypeptidase Y gave Leu-275 as the C-terminus of both the canine and bovine proteins. Mass spectral analysis of the canine protein showed the C-terminus at Arg-276 with a minor sequence extending to His-279, as predicted by amino acid sequencing after cyanogen bromide cleavage. In sum, the carboxy terminus is near His-279 in the canine protein, and, by analogy, near Met-279 in the human 18 kd protein. Based on the aforementioned results, there appear to be truncated C-terminal forms of the protein as well as truncated or staggered N-termini, depending on the particular preparation and species. It is accordingly postulated by the inventors herein that there are probably a number of C-termini for a particular species.

F. Synthetic Peptides

Various synthetic peptides based on the human 5 kd protein of the 10K mixture have been synthesized using standard techniques. Referring now to FIG. 15, the following peptides have been synthesized by the inventors herein: (1) 19-69, i.e., beginning at Phe-19 and ending at Gly-69; (2) 29-69, i.e., beginning at Lys-29 and ending at Gly-69; and (3) 19-56, i.e., beginning at Phe-19 and ending at Ser-56. After solubilization, each of the peptides was purified. A preferred method of purification is gel filtration using LH-60 columns in a solution of chloroform and methanol (1:1 v/v) containing 0.5% HCl. Each of the synthetic peptides was tested for in vitro and in vivo activity, with the following results:

In vitro activity: the procedure of section D.9 was used to evaluate the in vitro activity of the synthetic peptides described above.

Peptide 29-69 was ineffective in phospholipid film spreading in vitro, and, as might be expected from this result, was also ineffective in premature rabbit lungs. The N-terminal amino acids would thus appear to be required for maximal activity.

Peptide 19-69, a C-terminal extended peptide, was quite effective in both decreasing the surface tension of an air-water interface in vitro and in effecting reasonable lung function in animals (see Table 1). In Table 5, $P_{ins}$ is a measure of how effective the surfactant formulation is in lowering surface tension in the lungs. This decreased tension is manifested by a decreased pressure of inspired oxygen. Peptide 19-69 was quite effective compared to the saline control solution, and nearly as effective as the rabbit surfactant positive control. It should be noted that the native 5 kd protein is as effective as the surfactant control.

Peptide 19-56 was found to be as effective in vivo as native surfactant. In fact, in certain animal experiments, the $F_{ins}$ was lower in the animals treated with 19-56 than in the surfactant control. In all cases (see Table 2), the phospholipid mixture was DPPC:egg PG (7:3, w/w) and the ratio of PL to protein was 10:1. It is preferable that the peptide be administered in conjunction with additional lipids (see Section B.7) and, accordingly, in the studies summarized in Table 6, 10 wt. % palmitic acid was incorporated into the formulations. Thus, the formula was DPPC/PG:Peptide:fatty Acid in a weight ratio of about 10:1:1:1.

Other peptides which the inventors herein believe may be useful in the present method are the 27-56, 25-56, 23-56 and 21-56 peptides of the human 5 kd protein shown in FIG. 15.

TABLE 5

| | $P_{ins}$ | | | |
|---|---|---|---|---|
| | 10 min. | 20 min. | 30 min. | N |
| Rabbit Surfactant | 25 | 23 | 20 | 6 |
| SP 5K 10:1 | 27 | 22.5 | 20 | 5 |
| 19-69 | 28 | 24 | 22 | 3 |

TABLE 5-continued

| | $P_{ins}$ | | | |
|---|---|---|---|---|
| | 10 min. | 20 min. | 30 min. | N |
| 10:1 Sodium Chloride | 35 | 34 | 33 | 4 |

$P_{ins}$ values at 10, 20 and 30 minutes refer to the inspiratory pressures (cm $H_2O$) required to maintain tidal volumes in the lung of 6-7 mls/kg body weight. (The lower the pressure on the ventilator, the better.)

TABLE 6

Five different experiments were carried out in vivo. The numbers refer to pressures, Pins, at 30 minutes. This is the last time point in Table 1.

| Study # | Surfactant | NaCl | 19-56 |
|---|---|---|---|
| 119 | 22 | 0 | 22 |
| 120 | 16.5 | 26 | 15 |
| 121 | 19 | 33 | 16 |
| 122 | 16.5 | 33 | 15 |
| 123 | 0 | 32 | 15.5 |
| X | 18.5 | 31 | 16.7 |

The 0 refers to a pneumothorax before the end of the experiment. In all cases, 19-56 synthetic peptide was mixed with PL:Palmitic acid:syn pep (10:1:1) by weight. The phospholipid (PL) is DPPC:PG (7:3) by weight.

What is claimed is:

1. A mammalian alveolar surfactant protein (ASP) substantially free of impurities having a monomeric molecular weight of about 18 kd, as determined by polyacrylamide gel electrophoresis under nonreducing conditions.

2. The ASP of claim 1 which has an N-terminal amino acid sequence of:

Leu-Pro-Ile-Pro-Leu-Pro-Tyr-Cys-Trp-Leu-Cys-Arg-Thr-Leu-Ile-Lys-Arg-Ile-Gln-Ala-Met-Ile-Pro-Lys-Gly-Val-Leu-Ala-Val-Thr-Val-Gly-Gln-.

3. The ASP of claim 1 which has an N-terminal amino acid sequence of:

Phe-Pro-Ile-Pro-Leu-Pro-Tye-Cys-Trp-Lue-Cys-Arg-Thr-Lue-Ile-Lys-Arg-Ile-Gln-Ala-Met-Ile-Pro-Lys-Gly-Val-Leu-Ala-Val-Thr-?-Gly-Gln-.

4. The ASP of claim 1 which has the amino acid sequence depicted at positions 1-79 inclusive of FIG. 1.

5. The ASP of claim 1 which has the amino acid sequence depicted at positions 201-276 inclusive of FIG. 2.

6. A mammalian alveolar surfactant protein (ASP) which is a synthetic peptide having an amino acid sequence selected from the group consisting of the following:

amino acids 19-69 of FIG. 15;
amino acids 21-56 of FIG. 15;
amino acids 23-56 of FIG. 15;
amino acids 25-56 of FIG. 15;
amino acids 27-56 of FIG. 15;
amino acids 29-69 of FIG. 15; and
amino acids 19-56 of FIG. 15.

7. A pharmaceutical composition effective in treating respiratory distress syndrome (RDS) in mammals, which composition comprises the ASP of claim 1 in admixture with a pharmaceutically acceptable excipient.

8. A pharmaceutical composition effective in treating respiratory distress syndrome (RDS) in mammals, which composition comprises the ASP of claim 4 in admixture with a pharmaceutically acceptable excipient.

9. A pharmaceutical composition effective in treating respiratory distress syndrome (RDS) in mammals, which composition comprises the ASP of claim 5 in admixture with a pharmaceutically acceptable excipient.

* * * * *

UNITED STATES PATENT AND TRADEMARK OFFICE

CERTIFICATE OF CORRECTION

PATENT NO. : 5,430,020

DATED : July 4, 1995

INVENTOR(S) : James W. Schilling, Jr.; Robert T. White; Barbara Cordell; and Bradley J. Benson It is certified that error appears in the above-identified patent and that said Letters Patent is hereby corrected as shown below:

In the amino acid sequence listed in Claim 3, at column 28, lines 36-38:

(1) The seventh (7th) amino acid, "Tyr" has been misspelled as "Tye"; please delete "Tye" and substitute therefor - - Tyr - -.

(2) The tenth (10th) amino acid, "Leu" has been misspelled as "Lue"; please delete "Lue" and substitute therefor - - Leu - -.

(3) The fourteenth (14th) amino acid, "Leu" has been misspelled as "Lue"; please delete "Lue" and substitute therefor - - Leu - -.

Signed and Sealed this

Seventeenth Day of October, 1995

Attest:

Bruce Lehman

BRUCE LEHMAN

Attesting Officer

*Commissioner of Patents and Trademarks*